United States Patent [19]
Garrels

[11] Patent Number: 5,882,495
[45] Date of Patent: Mar. 16, 1999

[54] ELECTROPHORESIS SYSTEM

[75] Inventor: James I. Garrels, Beverly, Mass.

[73] Assignee: Proteome, Inc., Beverly, Mass.

[21] Appl. No.: 745,525

[22] Filed: Nov. 12, 1996

[51] Int. Cl.[6] .................................................. G01N 27/26
[52] U.S. Cl. .......................... 204/456; 204/462; 204/463; 204/464; 204/465; 204/606; 204/613; 204/615
[58] Field of Search .................................. 204/456, 465, 204/466, 467, 606, 615, 616, 618, 619, 620

[56] References Cited

U.S. PATENT DOCUMENTS

| | | | |
|---|---|---|---|
| 3,932,265 | 1/1976 | Hoefer | 204/619 |
| 3,964,992 | 6/1976 | Krotz | 422/82.01 |
| 3,980,540 | 9/1976 | Hoefer | 204/467 |
| 4,560,459 | 12/1985 | Hoefer | 204/467 |
| 4,612,106 | 9/1986 | Kromer et al. | 204/618 |
| 4,663,015 | 5/1987 | Sleeter et al. | 204/618 |
| 4,747,919 | 5/1988 | Anderson | 204/455 |
| 4,874,490 | 10/1989 | Hochstrasser | 204/467 |
| 4,915,811 | 4/1990 | Yamamoto et al. | 204/619 |
| 4,954,236 | 9/1990 | Kushner et al. | 204/466 |
| 5,188,790 | 2/1993 | Magnant | 264/219 |
| 5,192,408 | 3/1993 | Scott | 264/219 |
| 5,338,426 | 8/1994 | Shiguera et al. | 204/461 |
| 5,443,704 | 8/1995 | Kirkpatrick et al. | 204/620 |
| 5,472,589 | 12/1995 | Jacobs | 204/616 |

FOREIGN PATENT DOCUMENTS 38 39 948 A1   11/1988   Germany .

OTHER PUBLICATIONS

WPIDS abstract of Rogner (DE 3839948 A), May 3, 1989.
Oxford GlycoSystems, Inc., Product Information Re: Investigator™ Electrophorsis 2–D System, brochure Date (year) not provided–unknown.

Bio–Road, "Mini 2–D Electrophoresis Cell", brochure p. 159 Date (year) not provided–unknown.

Pharmacia Biotech, "PhastSystem Electrophoresis", brochure pp. 473–474 Date (year) not provided–unknown.

Novex, "ThermoFlow ETC Unit", brochure pp. 36–37, 1996–1997.

Hoefer Scientific Instruments, "The SE 200 Series", brochure, 1994 month unknown.

Hoefer Scientific Instruments, "Vertical Slab Gel Units", brochure 1993 month unknown.

Hoefer Scientific Instruments, "SE600 Series Cooled Vertical Slab Units", brochure 1991 month unknown.

Oxford GlycoSystems, Inc., Product Information Re: Investigator™ Electrophoresis 2–D System, pp. 5–7, brochuer Date (year) not provided–unknown.

Primary Examiner—William H. Beisner
Assistant Examiner—Alex Noguerola
Attorney, Agent, or Firm—Linda M. Buckley; Robert L. Buchanan

[57] ABSTRACT

The present invention provides electrophoresis systems and methods for forming at least one gel therein and for conducting electrophoresis on the gel without removing the gel from the electrophoresis system. The systems of the present invention include an electrophoresis platform which is a surface onto which one or more electrophoresis gels can be cast, and at least one gel casting/electrophoresis member for use in casting at least one gel on the electrophoresis platform and conducting electrophoresis on the gel. The present invention also includes optional members specific to other stages of the electrophoresis process, including a gel staining member and a gel drying member.

36 Claims, 12 Drawing Sheets

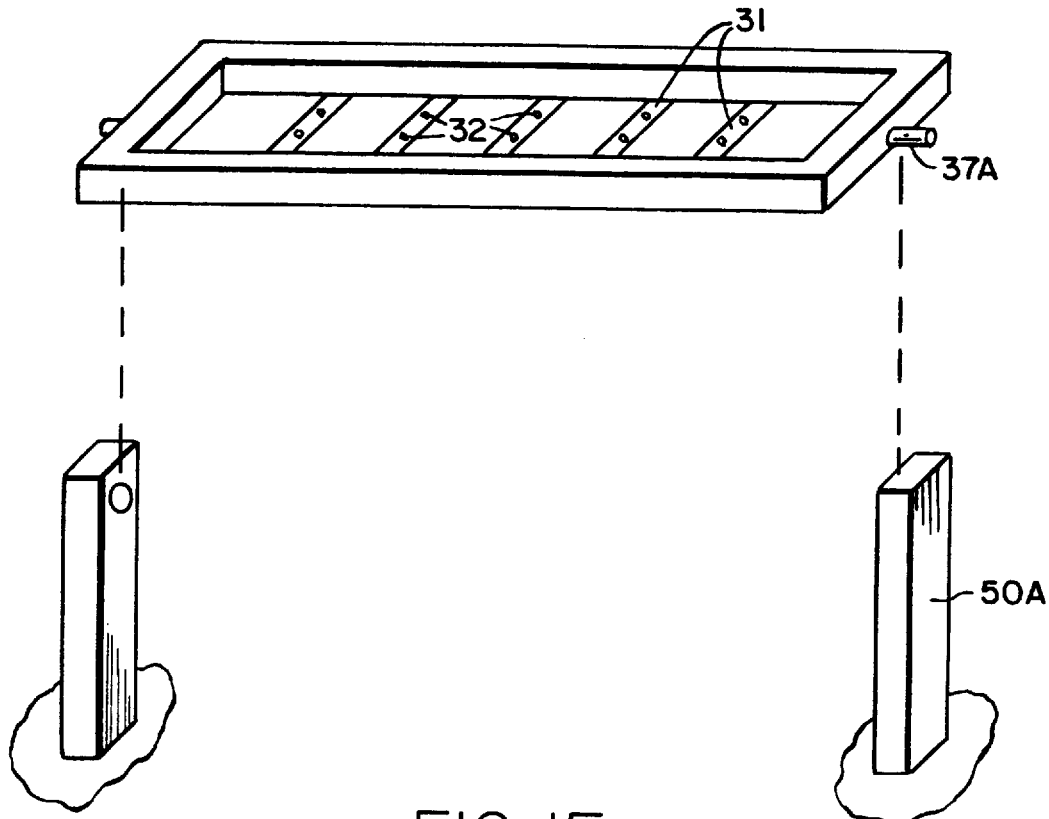
FIG. IE
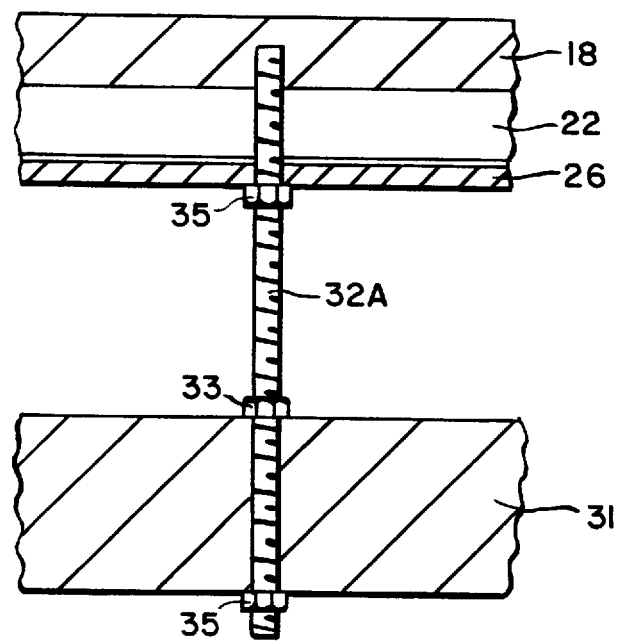
FIG. IF

ELECTROPHORESIS SYSTEM

BACKGROUND OF INVENTION

This invention relates to electrophoresis systems and methods for the separation of complex mixtures of charged molecules, particularly complex biological mixtures, with higher resolution and higher throughput.

Two-dimensional gel electrophoresis is the method of choice for analysis of complex protein mixtures, but its level of resolution is not yet adequate to detect many of the protein components from cells or tissues. There remains a need to detect more of the protein components of cells, tissues, and other complex biological mixtures. Electrophoretic separation on large format gels, e.g., greater than about 20 cm by 20 cm, can greatly improve resolution. However, the advantages of increased resolution resulting from large format gels is typically offset by the difficulties encountered in handling such large gels in conventional systems. Furthermore, known methods of electrophoresis are often limited by convenience so that routine analysis of large numbers of samples is not practical.

Accordingly, electrophoresis systems that will enable casting large format gels of controlled thickness, electrophoresis of multiple large format gels within a reasonable time without excess heat generation, and convenient manipulation of the gels through all steps of the electrophoresis process thereby providing greater resolution and higher consistency of results are being sought.

SUMMARY OF INVENTION

The present invention provides an electrophoresis system for forming at least one gel and for conducting electrophoresis on the gel without removing the gel from the system. Staining and/or drying of the gel or gels are preferably carried out in the system. For example, it is particularly advantageous in the case of large format gels and in the case of multiple gels where reproducibility and consistency are particularly important to carry out most, if not all, steps of the electrophoresis process, i.e., gel casting, electrophoresis, staining and drying, without removing the gel from the system.

The systems of the present invention comprise an electrophoresis platform which is a surface onto which one or more electrophoresis gels can be cast, and at least one gel casting/electrophoresis member for use in casting a gel on the electrophoresis platform and conducting electrophoresis on the gel. The present invention also provides optional attachments specific to other stages of the electrophoresis process, including a gel staining member and a gel drying member.

In one embodiment, the present invention provides an electrophoresis system for forming at least one gel and for conducting electrophoresis on the gel without removing the gel from the system. The system comprises an electrophoresis platform defining a first nonconductive surface which is adapted to receive at least one gel casting/electrophoresis member defining a second nonconductive surface. When the gel casting/electrophoresis member is sealably disposed on the first nonconductive surface, a space is defined between the first and second nonconductive surfaces for forming a gel.

The electrophoresis platform is tiltable between horizontal and vertical positions. In one preferred embodiment, the electrophoresis platform is tiltable through at least 90 degrees.

In preferred embodiments of the present invention, the system further comprises a gel staining member. In such embodiments, the electrophoresis system is configured to receive at least one gel staining member for staining a gel disposed thereon without removing the gel from the system after electrophoresis has been conducted. The gel staining member defines a third surface, and when sealably disposed on the first nonconductive surface of the electrophoresis platform over a gel, a space is defined between the first and third surfaces, as well as between the third surface and the gel, for containing a staining agent for the gel. A gel staining member is not required to stain a gel without removing it from the electrophoresis system of the present invention. When a gel staining member is not used, the electrophoresis platform is configured to confine the staining fluids.

In particularly preferred embodiments of the present invention, the electrophoresis system is configured to receive multiple gels which can be run at the same time and, optionally, stained and/or dried at the same time.

In one particularly preferred embodiment, the system of the present invention for forming at least one gel and for conducting electrophoresis on the gel without removing the gel from the system comprises:

(a) an electrophoresis platform defining a first nonconductive surface, wherein the electrophoresis platform is tiltable between horizontal and vertical positions;

(b) at least one gel casting/electrophoresis member defining a second nonconductive surface and configured for removable and sealable attachment to the first surface, wherein the gel casting/electrophoresis member when sealably disposed on the first surface defines a space between the first and second surfaces for forming the gel and, further wherein the gel casting/electrophoresis member comprises a first end and a second end, the second end being lower when the electrophoresis platform is in a vertical position;

(c) at least one first buffer chamber capable of communicating with the first end and at least one second buffer chamber capable of communicating with the second end; and (d) at least one first and second electrodes insertable into the first and second buffer chambers respectively, the electrodes connectable to a power supply for establishing an electromotive force for inducing electrophoretic action.

The electrophoresis platforms of the present invention preferably further comprise a support member disposed below the first nonconductive layer to provide a flat, rigid layer with high heat conductivity.

Preferred nonconducting materials for use in the present invention comprise glass or plastics such as acrylic or polycarbonate. Glass is an especially preferred nonconducting material for the first surface of the electrophoresis platform and the second surface defined by the gel staining member. Although glass is preferred other useful materials include suitable plastics. Preferred heat conducting materials include aluminum, stainless steel and other nonrusting or nonoxidizing metals or metal alloys.

The electrophoresis systems of the present invention preferably further comprise one or more cooling systems to regulate the temperature of the first and second surfaces defined by the electrophoresis platform and gel casting/electrophoresis members respectively, for example, by the circulation of a heat transfer fluid adjacent the first and/or second surfaces. In one embodiment of the present invention, the metal support member of the electrophoresis platform further comprises a cooling system for the first surface. Such metal support member and cooling system are sometimes hereinafter collectively referred to as a metal base assembly. The support member or metal base assembly is of sufficient rigidity to support the first nonconductive surface without bending. In preferred embodiments, the cooling system for the second nonconductive surface is disposed adjacent thereto in the gel casting/electrophoresis member.

The electrophoresis systems of the present invention optionally further comprise an agitation system to move the electrophoresis platform in a predetermined manner, for example, in a rocking and/or oscillatory manner.

The gel casting/electrophoresis member, in preferred embodiments, further comprises a holding member in which the second nonconductive surface can be removably disposed. In preferred embodiments, a cooling system for the second nonconductive surface is disposed in the holding member. The holding member is provided with a resilient fluid-impermeable material disposed adjacent and surrounding the perimeter of the second nonconducting surface, the resilient fluid-impermeable material being capable of providing sealing contact with the first surface of the electrophoresis platform. The resilient fluid-impermeable material in some embodiments comprises a continuous gasket disposed in a groove on the holding member. Preferred resilient fluid-impermeable materials are substantially inert to the conditions of electrophoresis and include silicone rubber, gum rubber, Buna-N, ethylene propylene, and viton.

The first and second ends of one preferred gel casting/electrophoresis member are each provided with at least one opening to provide communication among the gel, the first and second buffer chambers and the electrodes. Preferably the opening in the lower second end is removably sealable.

The systems of the present invention optionally further comprise at least one gel staining member for staining the gel after electrophoresis has been conducted without removing the gel from the electrophoresis system. The gel staining member defines a third surface and is configured for removable and sealable attachment over a gel disposed on the first surface. When the gel staining member is sealably disposed on the first surface of the electrophoresis platform over a gel, it defines a space between the third surface and the gel for containing a staining agent for the gel. The gel staining member further comprises a first and a second end. In one embodiment, the gel staining member comprises a rigid plastic member having disposed therein a central hollow area or recess defining the third surface and gel containment space, and may further comprise a first staining agent reservoir communicating with the first end and a second staining agent reservoir communicating with the second. Both staining agent reservoirs communicate with the central recess.

The systems of the present invention optionally further comprise a gel drying member for drying at least one gel after electrophoresis has been conducted without removing the gel from the system, the gel drying member defining a water permeable surface and configured for removable and sealable attachment over at least one gel disposed on the first nonconductive surface, wherein the permeable surface of the gel drying member when sealably disposed on the first nonconductive surface over the gel contacts the gel. In preferred embodiments, the gel drying member further comprises a rigid plastic sheet disposed over the permeable surface, the plastic sheet comprising at least one port open to the permeable surface and to the atmosphere, and a non-rigid seal around the perimeter of the rigid plastic sheet, the seal being capable of providing a seal between the rigid plastic sheet and the first nonconductive surface.

The present invention also provides electrophoretic methods for use in the innovative systems of the present invention. One such method comprises:

(a) forming the gel between the first surface of the electrophoresis platform and the second surface of the gel casting/electrophoresis member wherein the electrophoresis platform is disposed in a vertical position;

(b) positioning the electrophoresis platform in the desired position, i.e., a vertical position, a horizontal position, or a position between vertical and horizontal;

(c) applying the mixture to be separated to the gel; and (d) separating the mixture by electrophoresis.

When the sample is in liquid form, it is provided to the gel with the electrophoresis platform in a vertical position. When the sample is not in liquid form, e.g., is another gel, it can be provided to the gel with the electrophoresis platform in any position, although a position between horizontal and vertical is typically more convenient.

The method of the present invention optionally includes a staining step for staining the gel after electrophoresis has been conducted without removing the gel from the system. One such method which includes staining comprises the further steps:

(e) removing the gel casting/electrophoresis member;

(f) sealably disposing the gel staining member over the gel; and (g) providing at least one staining agent to the space between the first and third surfaces.

The method of the present invention may further comprise an agitation step, wherein the electrophoresis platform is agitated to facilitate staining.

The methods of the present invention optionally includes a drying step for drying the gel after electrophoresis has been conducted without removing the gel from the system. One such method comprises the further steps:

(h) sealably disposing the gel drying member over a gel disposed on the first nonconductive surface wherein the water permeable surface contacts the gel; and (i) providing heat and vacuum to the gel to cause water to pass from the gel through the water permeable surface.

The systems and methods of the present invention for two-dimensional gel electrophoresis provide significant improvements, both in resolution of materials separated in complex mixtures of proteins and protein fragments and in convenience of use.

Instead of forming a gel between two surfaces of approximately equal size as is conventionally done, the systems of the present invention incorporate an electrophoresis platform upon which from one to multiple gels can be cast. A gel casting/electrophoresis member is sealably disposed on the first nonconductive surface of the electrophoresis platform, e.g., clamped against or held by vacuum to the electrophoresis platform to form a space or mold in which the gel is cast. The same gel casting/electrophoresis member is used during the electrophoresis step. Other apparatus of the present invention can be sealably disposed on the electrophoresis platform for the steps of gel staining and gel drying.

By using a large electrophoresis platform as one of the electrophoresis surfaces, larger gels can be run and the inconvenience of handling large gels is greatly diminished. Furthermore, multiple gels can be run at one time. The electrophoresis systems of the present invention provide novel methods for casting gels, staining gels, and drying gels. These systems also lead to simplification of the design of the accessory equipment needed to carry out these steps.

The systems and methods of the present invention overcome many of the disadvantages associated with known electrophoresis systems, particularly in terms of resolution and reproducibility. One important advantage resides in the ability to cast large gels of controlled thickness. Another major advantage of electrophoresis systems in accordance with the present invention is the ability to process thin gels of large width and length without removal from the electrophoresis platform. The electrophoresis systems of the present invention have the further advantage of simplicity which provides convenience of use and greater reproducibility.

BRIEF DESCRIPTION OF THE DRAWINGS

FIG. 1E is an exploded perspective view of another embodiment of a cradle assembly and support frame in accordance with the present invention.

FIG. 1F is an enlarged cross section view of an electrophoresis platform connected to a cradle assembly by means of leveling screws, leveling nuts and locking nuts.

DETAILED DESCRIPTION OF THE INVENTION

Figure 1A:
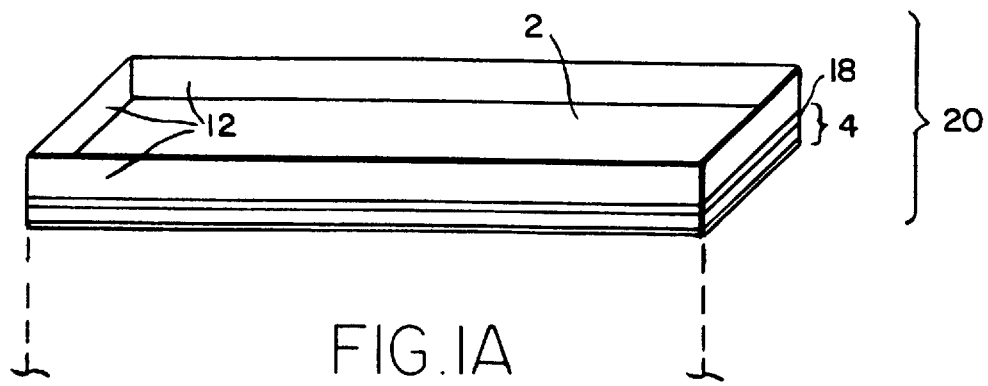
FIGS. 1A to C show an exploded perspective view of one embodiment of an electrophoresis system of the present invention comprising an electrophoresis platform, a cradle assembly and a support frame.

Although the electrophoresis systems and methods of the present invention are primarily illustrated by those which have been adapted for conducting electrophoresis on multiple gels and/or large format gels, it will be appreciated by those skilled in the art that such systems may also be used for conducting electrophoresis on a single gel of any size. It will also be appreciated by the skilled artisan that the invention is not limited in its application to the details of the construction and the arrangements of components set forth in the following description or illustrated in the drawings. The electrophoresis systems of the present invention include other embodiments and the methods of the present invention can be practiced or carried out in various ways.

The electrophoresis systems of the present invention comprise an electrophoresis platform on which gel(s) are cast and electrophoresis is carried out on the gel(s). Gels are formed on the electrophoresis platform by use of one or more gel casting/electrophoresis members of the present invention. The gel casting/electrophoresis member is adapted for sealable attachment to the electrophoresis platform so that a gel can be formed between the electrophoresis platform and the gel casting/electrophoresis member. Sample is then applied to the gel and electrophoresis is carried out on the gel without removing it from the platform. After electrophoresis, the gel casting member can be replaced with a gel staining member of the present invention which is used to contain staining fluids above the gel. After staining or directly after electrophoresis, a gel drying member of the present invention can be placed over the gel to dry the gel in place on the electrophoresis platform.

In preferred embodiments, the electrophoresis platform comprises a flat, non-conductive, temperature-controlled surface which is capable of containing a liquid, for example, by surrounding the platform with walls to form a tray-like member. In a particularly preferred embodiment, the nonconductive surface of the electrophoresis platform comprises a glass plate which is in turn supported by a metal base assembly comprising a metal support member or plate which comprises a cooling system to help regulate the temperature of the first nonconductive surface. The metal base assembly comprises channels designed to carry fluid for cooling the metal plate during electrophoresis or for heating the metal plate during gel drying to thereby control the temperature of the first nonconductive surface. In some embodiments, the metal base assembly is provided with heating coils or tapes.

An electrophoresis platform of the present invention is movably mounted in or on a support structure which allows the platform to be tilted through at least 90 degrees and which can provide a rocking or oscillatory motion when in the horizontal position. In one preferred embodiment the electrophoresis platform is typically large enough to accommodate the production of 6 to 8 two-dimensional gels at one time.

The configuration and dimensions of electrophoresis platforms for use in the methods of the present invention are determined by the desired number and size of gels to be run. Gels from about 20 to about 50 cm in length and in width are conveniently cast and run and, if desired, stained and dried on an electrophoresis platform about 24 inches (front to back) and 96 inches long (side to side). However, any dimension sufficiently large to run multiple gels yet not so large as to be impractical in changing and maintaining the position of the electrophoresis platform are acceptable.

The first step of the electrophoresis process, gel casting, is typically performed with the electrophoresis platform in a vertical position. The gel casting members of the present invention are configured for sealable attachment to the platform and, when attached thereto, to provide a space for forming the gel and to provide electrodes and buffer to the gel for carrying out electrophoresis.

One preferred gel casting/electrophoresis member of the present invention comprises a rigid, non-conductive member, e.g., a sheet of plastic material, with a recess formed therein to hold a second nonconductive surface, preferably a glass plate. The rigid nonconductive member is of sufficient rigidity to hold the glass plate without bending. Rigidity can be achieved by the thickness of the material, by reinforcing members, or a combination of both. In some embodiments, the rigid nonconductive member is provided with two or more recesses so that two or more gels can be formed in a single gel casting/electrophoresis member. The rigid recessed member is configured so that the second nonconductive surface can be sealably disposed in the recess. In preferred embodiments, the recess is provided with channels which can provide direct contact of a temperature controlled fluid with the second nonconductive surface. The thickness of the rigid recessed member is selected to provide the desired rigidity, space to form the recess and to provide cooling channels for a temperature control fluid. The glass plate (second nonconductive surface) is disposed in the recess and held against the cooling channels of the rigid recessed member, for example, by negative pressure created by a vacuum pump, and is sealed, e.g., by an O-ring mounted between the glass plate and the rigid recessed member. In one preferred embodiment, the perimeter of the rigid recessed member adjacent to and outside the glass plate is provided with at least one O-ring groove to receive an O-ring which, when the gel casting/electrophoresis member is disposed on the electrophoresis platform, provides sealing contact. In preferred embodiments, the gel casting/electrophoresis member is sealably affixed to the electrophoresis platform by a vacuum created between the gel casting/electrophoresis member and the platform.

The shape and dimensions of the gel are determined by the space defined by the gel casting/electrophoresis member and the electrophoresis platform. The gel space need not be of constant thickness. For example, the gel casting/electrophoresis member may be configured to define a wedge-shaped space to provide a gel that is thinner at the bottom than the top, bottom referring to the bottom of the gel when the electrophoresis platform is in a vertical position. The gel casting/electrophoresis member with mounted glass plate facing the electrophoresis platform is sealably positioned, e.g., by clamping or by vacuum, on the first nonconductive surface of the electrophoresis platform thereby defining a space for forming a gel. The seal is made against the electrophoresis platform with, e.g., a second O-ring wherein the outer circumference of the rigid recessed member, in which a second O-ring groove is formed, forms the outer circumference of the space or mold into which the gel solution is poured prior to polymerization. The desired thickness of the gel is achieved by configuring the appropriate dimensions of the gel casting/electrophoresis member to hold the glass plate at a predetermined distance from the first nonconductive surface of the electrophoresis platform.

The gel casting/electrophoresis member is preferably provided with reservoirs for providing electrode buffer to the gel during electrophoresis. Such reservoirs are in some embodiments attachable near each end of the rigid recessed member or permanently affixed thereto. These reservoirs communicate with the gel via openings, e.g., slots, appropriately positioned in the gel casting/electrophoresis member. During the gel casting step, when the electrophoresis platform and attached gel casting/electrophoresis member(s) are in a vertical position, the opening(s) in the lower reservoir are sealed with a reversible sealant, such as tape, and gel solution is poured into the space formed between the gel casting/electrophoresis member and the first surface of the electrophoresis platform.

After polymerization, the seal covering the lower opening is removed and the electrophoresis platform is placed in a horizontal, vertical or intermediate position for application of the sample to the gel at the end near the upper reservoir. After the sample is applied, electrode buffers are added to the reservoirs of the gel casting/electrophoresis member to form a conductive path between electrodes which are permanently fixed in the reservoirs or can be introduced into the upper and lower reservoirs just before electrophoresis. The seal covering the opening(s) in the lower reservoir during polymerization of the gel may be on the inner side of the opening, i.e., the surface which contacts the gel, or on the outer side of the opening, i.e., the side opposite the gel. When the seal is on the inner side, it is cut to open it. In preferred embodiments, gel is removed from the area just beneath the opening. Electrophoresis is performed on the gel in the gel casting/electrophoresis member without further handling of the gel by causing a current to flow between the electrodes. Conventional electrodes are suitable for use in the present invention.

Electrophoresis can be carried out with the electrophoresis platform in a horizontal, vertical or intermediate position so long as the reservoirs are configured to retain buffer solution when in that position. In the case of liquid samples, sample application and electrophoresis are carried out with the platform in a vertical position.

After electrophoresis is complete, the gel casting/electrophoresis member(s) are removed, preferably with the electrophoresis platform in a horizontal position, leaving the gel(s) in place on the surface of the electrophoresis platform. Gel staining can be carried out on the electrophoresis platform by adding at least one staining fluid to the electrophoresis platform or by placing gel staining member(s) of the present invention over the gel(s) to provide staining fluids to the gels, and to confine the staining fluids. In either embodiment, the electrophoresis system of the present invention enables fluids to be changed simultaneously for all gels on the electrophoresis platform, thereby assuring reproducibility of staining conditions. In typical staining operations, multiple fluids are used in sequential staining steps.

In one preferred embodiment, the staining member of the present invention comprises a flat sheet of rigid material, e.g., plastic, with a recess formed therein to create a staining chamber. The staining member is sealably attachable to the platform. In one embodiment, the recess is surrounded by at least one groove in which an O-ring is disposed to provide a seal with the first nonconductive surface of the electrophoresis platform. The staining member is positioned over a gel with the recess facing the gel, and is then sealably disposed on the electrophoresis platform over the gel either by use of mechanical means or by a vacuum created between the staining member and the electrophoresis platform.

The staining member is configured to constrain the gel within a space of limited volume, but contains enough space for movement of solution on all surfaces of the gel. The staining member further comprises reservoirs at each end to contain staining fluids, and these reservoirs communicate with the staining chamber. If preferred, staining is carried out while the electrophoresis platform is rocked by the agitation mechanism. In some embodiments, changing of staining fluids is achieved by tilting the electrophoresis platform to drain each fluid used away from the gel and removing it, e.g., by aspiration.

In other preferred embodiments, the walls surrounding the electrophoresis platform form a staining chamber without a staining apparatus. Agitation is applied through the rocking of the electrophoresis platform, and solutions are changed after tilting the electrophoresis platform to drain the solutions to one edge of the tray for removal by, e.g., aspiration. Using the entire electrophoresis platform for staining can be simpler than using a staining apparatus, but larger volumes of the staining fluids are required, thus increasing the cost of the process.

Gels, either stained or unstained, can be dried without removal from the electrophoresis platform by use of a gel drying member of the present invention. In one preferred embodiment, a gel is prepared for drying by placing thereunder a thin sheet of material having a nonadhesive surface, e.g., teflon, configured slightly larger than the gel while the gel is immersed in water or another liquid on the electrophoresis platform. The liquid is then removed from the platform and a material onto which the gel will be dried, e.g., a sheet of paper, is placed in contact with the upper surface of the gel.

In one embodiment of the present invention, the gel drying member comprises a water permeable surface which is placed over the paper sheet to indirectly contact the gel. Heat and vacuum is applied to the gel to cause the water to pass through the water permeable surface.

In one preferred embodiment, the gel drying member of the present invention comprises a rigid sheet, preferably of plastic, with a recess formed in the underside, a sheet of porous plastic material is disposed in the recess and optionally channels are provided in the recess for vacuum dispersion and fitted with a port on the top for connection to a high vacuum line. The components of conventional gel drying apparatus can be adapted for use in the present invention.

In use, a gel drying member is placed over a gel on the non-adhesive surface and sealed to the electrophoresis platform by a non-rigid seal such as a sheet of silicone rubber which enables a drying member to move closer to the electrophoresis platform as the gel is dried. Vacuum is applied to a port in the apparatus by a vacuum pump, and heat can be applied through the temperature-control system of the electrophoresis platform thereby causing the water in the gel to be removed.

This invention comprises a movable surface, the electrophoresis platform, which accommodates multiple steps of electrophoresis, and one or more attachments which mount to the platform, specific to the particular steps of electrophoresis. Support for the electrophoresis platform is not limited to any particular configuration but the platform must be movable as described above.

Referring now to FIG. 1 there is shown one preferred embodiment of an electrophoresis platform 20 for use in the electrophoresis systems of the present invention. Electrophoresis platform 20, shown in FIG. 1A, provides a movable, temperature-controlled surface on which several steps of electrophoresis, including gel casting and gel electrophoresis, and if desired, gel staining and/or gel drying, can be performed. It is large enough to accommodate the processing of multiple gels during each step of the procedure. For example, the embodiment shown in FIG. 1 is about 2 feet by 8 feet, a convenient dimension for running 6 gels of 30 cm width or 4 gels of 40 cm width. Electrophoresis platform 20 comprises first nonconductive surface 2, such as glass, mounted on metal base assembly 4 which provides flatness and even temperature. Metal base assembly 4 is comprised of channels 6 to provide for circulation of a temperature-controlled liquid through inlet port 8 and outlet port 10 (see FIG. 2). In the embodiment shown, electrophoresis platform 20 is surrounded by walls 12 so that fluids can be contained on first nonconductive surface 2.

Services such as electrode buffer, vacuum, distilled water, cooling water, and waste removal as needed for the procedures carried out on the electrophoresis platform are readily provided by use of components and methods well known to the skilled artisan.

Figure 1B:
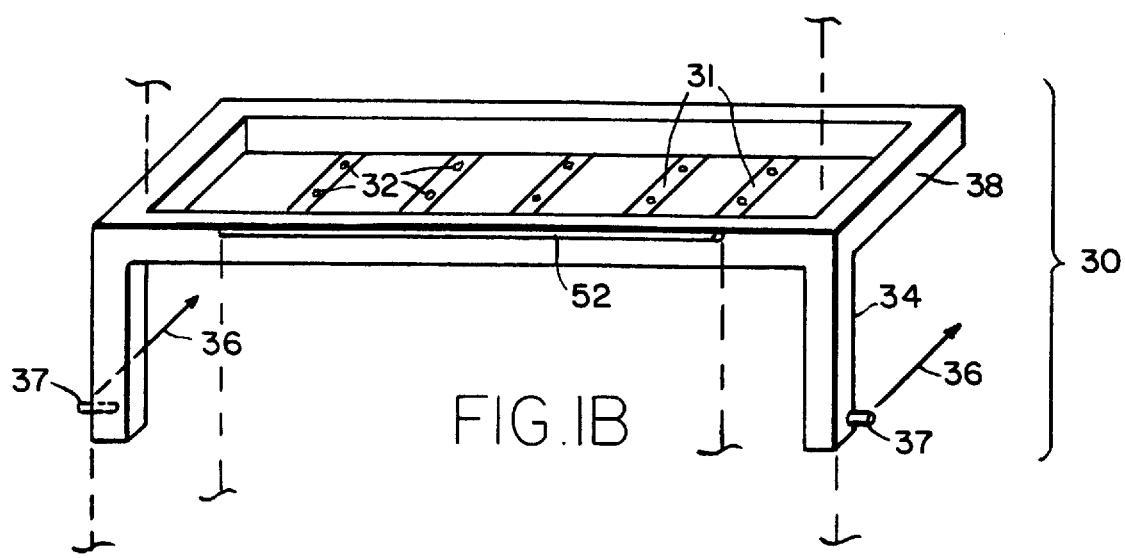
Figure 1C:
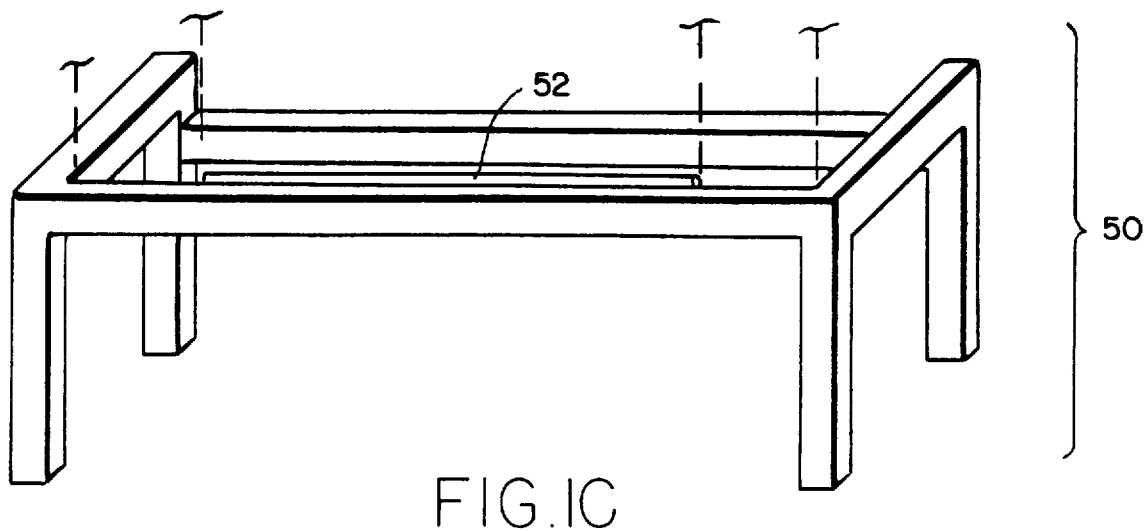

In the embodiment shown, electrophoresis platform 20 is mounted inside the frame formed by cradle assembly 30 and affixed to supports 31, shown in FIG. 1B, through a series of leveling screws 32A shown in FIG. 1F affixed to the bottom of metal base assembly 4. Screws 32A pass through openings 32 in support 31. Leveling nuts 33 and locking nuts 35 shown in FIG. 1F are used to perform the important function of leveling electrophoresis platform 20. Cradle assembly 30 is in turn mounted to support frame 50, shown in FIG. 1C, through hinge 52 on the front edge. Arm 34 projecting down from cradle 30 on a line below hinge 52 is connected through pin 37 to cable 36 which is in turn connected to a winch (not shown), thus comprising a lifting mechanism that can rotate cradle 30 about hinge 52 and hold it rigidly at any position between horizontal and vertical. An alternative embodiment to provide support for cradle assembly 30 is shown in FIG. 1E. Support members 50A are affixed to the floor or to a support base. In some embodiments, cradle 30 is provided with rails 49 shown in FIG. 1D for mounting hold-down assemblies 40, also shown in FIG. 1D.

Figure 1D:
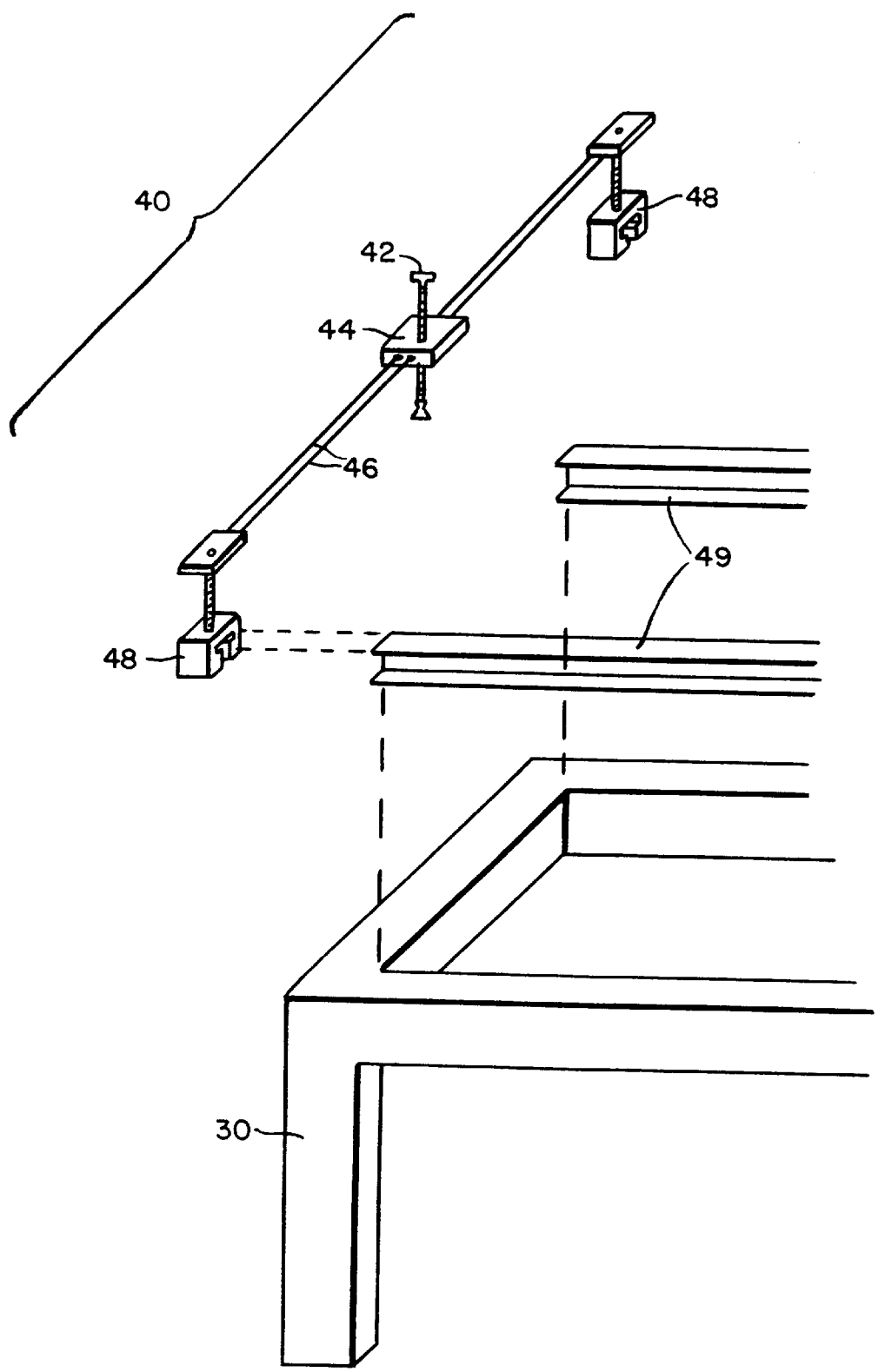
FIG. 1D is an exploded perspective view showing one end of the cradle assembly shown in FIG. 1B, together with one embodiment of a hold-down assembly of the present invention.

One preferred embodiment of a hold-down assembly useful in the practice of the present invention is shown in FIG. 1D. In some electrophoresis systems of the present invention, one or more hold-down assemblies 40 are used to removably affix gel casting/electrophoresis members and gel staining members as desired to electrophoresis platform 20. In the embodiment shown in FIG. 1D, hold-down assembly 40 extends from front to back across electrophoresis platform 20 and comprises hold-down bars 46, hold-down bar slider 44, thumbscrews 42, and rail sliders 48. When hold-down assemblies 40 are used, rails 49 are disposed along each length of the top edge of cradle assembly 30. Rails 49 receive rail sliders 48 of one or more hold-down assemblies 40 and enable hold-down assembly 40 to be moved along the length of cradle assembly 30 to the desired location on the platform.

Figure 1G:
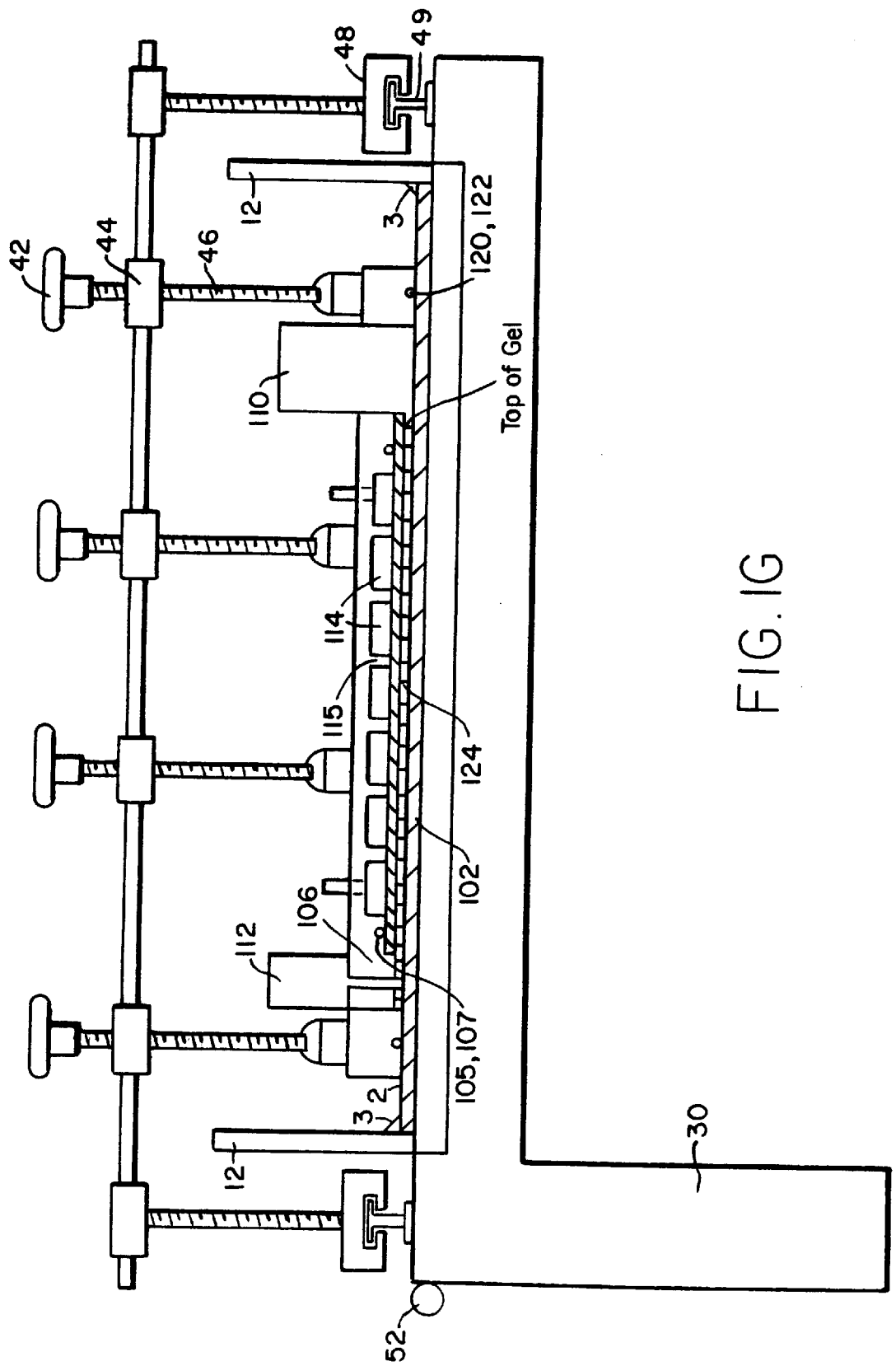
FIG. 1G is a schematic cross section view of an electrophoresis platform of the present invention disposed in a cradle assembly as shown in FIG. 1B and having disposed thereon a gel casting/electrophoresis member of the present invention within which has been formed a gel.

An enlarged schematic view of hold-down assembly 40 attached to metal base assembly 4 of electrophoresis platform 20 and to support member 31 of cradle assembly 30 is shown in FIG. 1G. In this view, hold-down assembly 40 is disposed over a gel casting/electrophoresis member 100 of the present invention and adjusted to affix member 100 to electrophoresis platform 20.

The pressure to hold gel casting/electrophoresis and gel staining members to electrophoresis platform 20 is provided by thumbscrews 42 mounted into sliders 44 which move along the hold-down bars 46. The bars themselves are mounted at each end to sliders 48 which move along rails 49 on the front and back edge of the cradle. Hold-down assembly 40 allows thumbscrews 42 to be positioned at any point above electrophoresis platform 20 and can provide sufficient force to clamp and seal gel casting/electrophoresis and gel staining attachments to the electrophoresis platform.

Figure 4A:
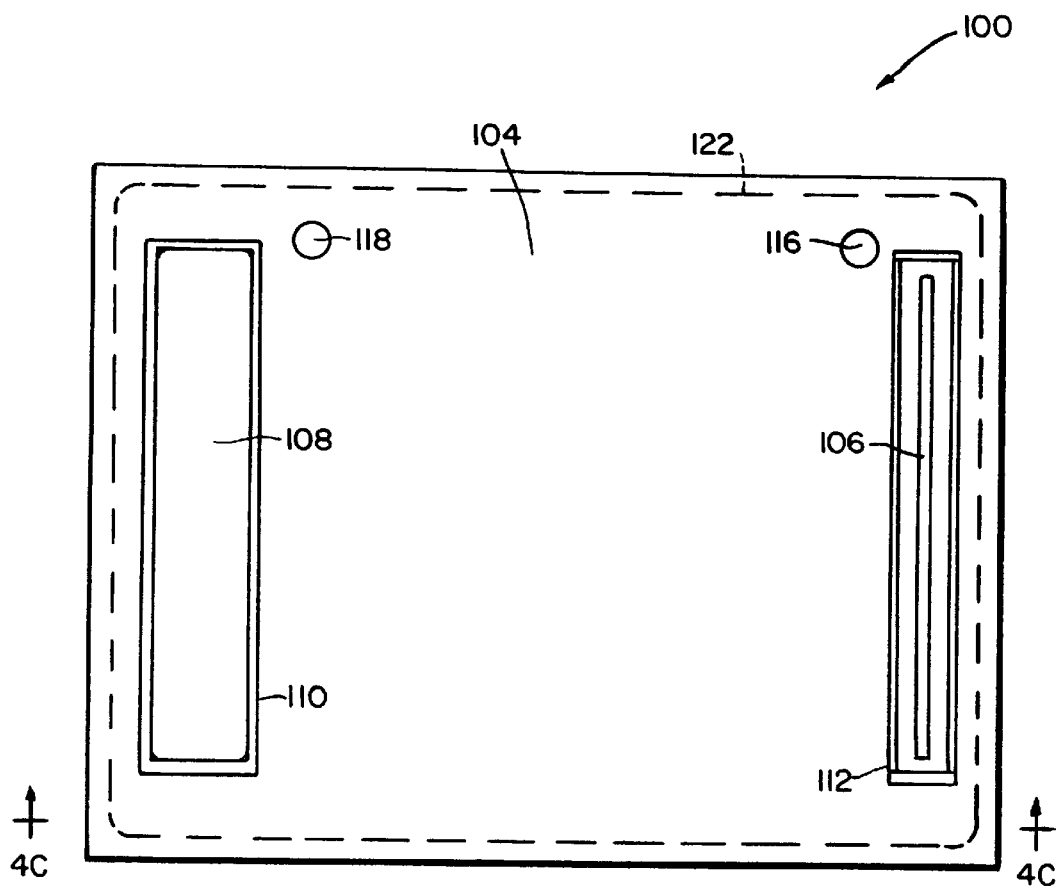
FIG. 4A is a top plan view of one embodiment of a gel casting/electrophoresis member of the present invention.
Figure 4C:
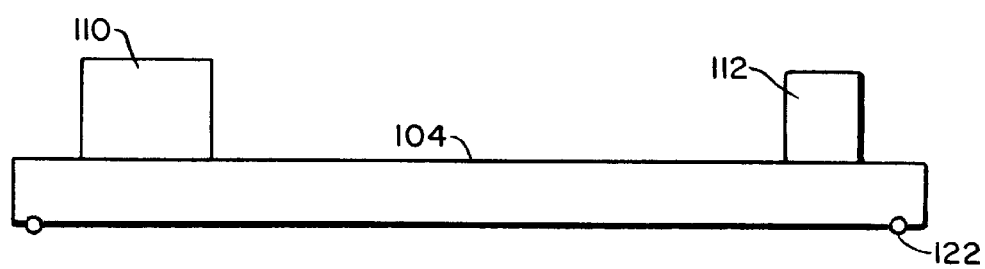
FIG. 4C is a section along 4C—4C of the gel casting/electrophoresis member shown in FIG. 4A.
Figure 4B:
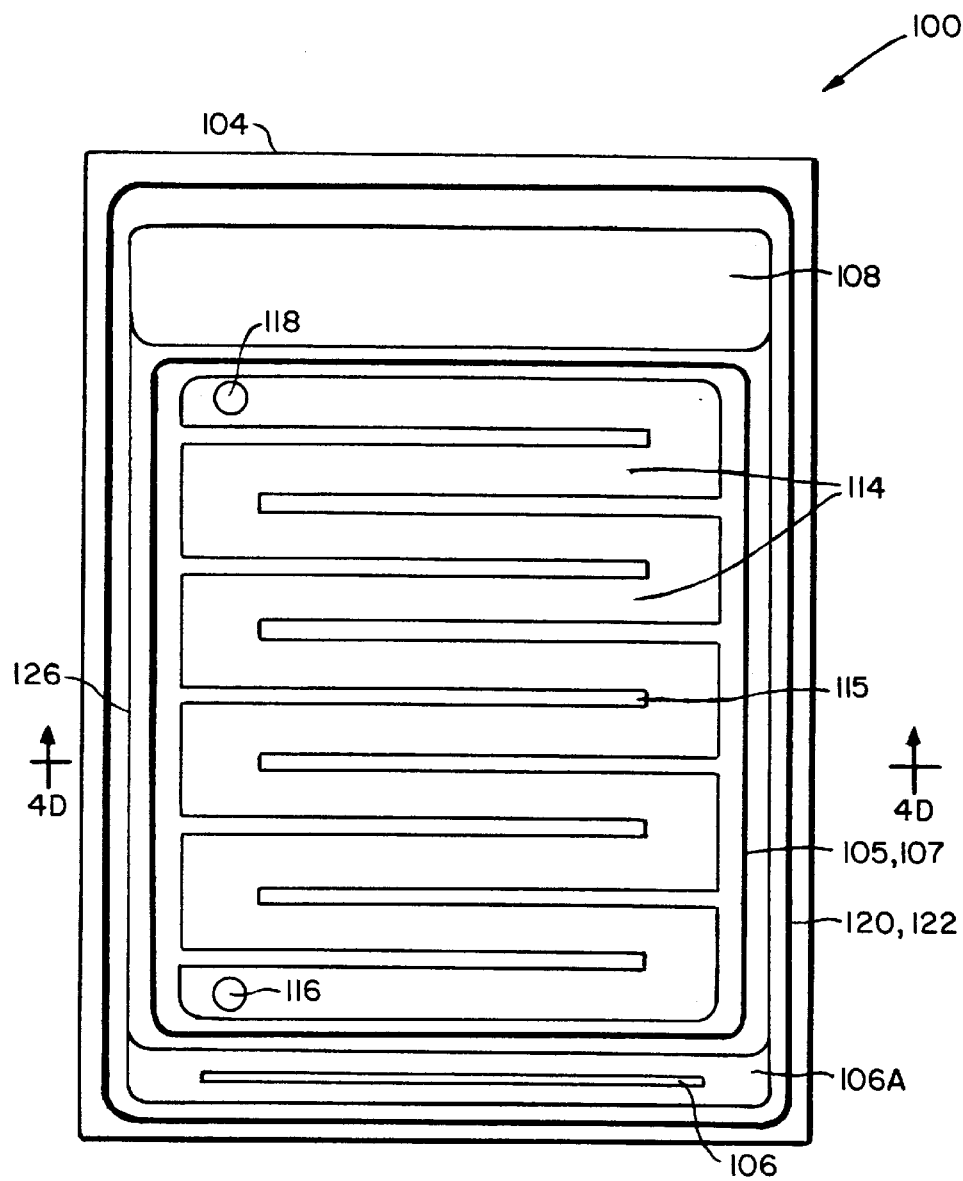
FIG. 4B is a bottom plan view of the gel casting/electrophoresis member shown in FIG. 4A.
Figure 5A:
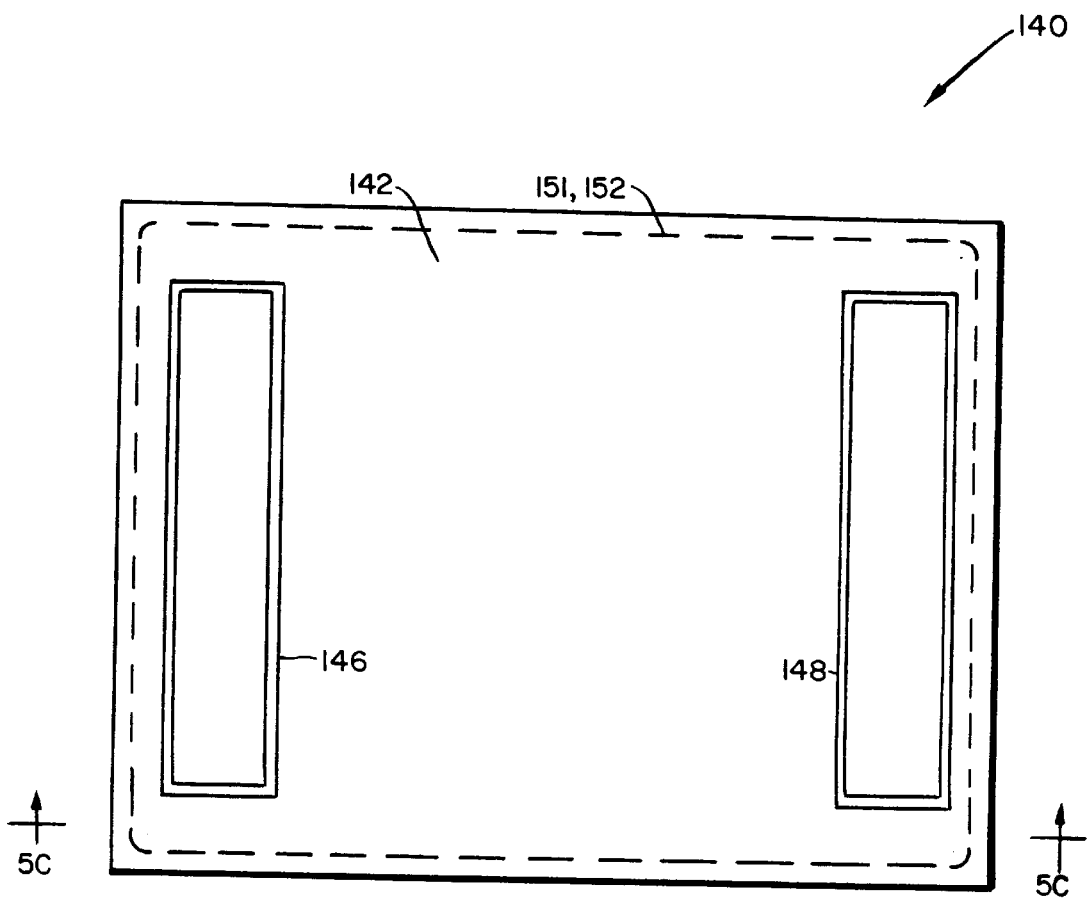
FIG. 5A is a top plan view of a rigid recessed member of one embodiment of a staining member in accordance with the present invention.
Figure 5C:
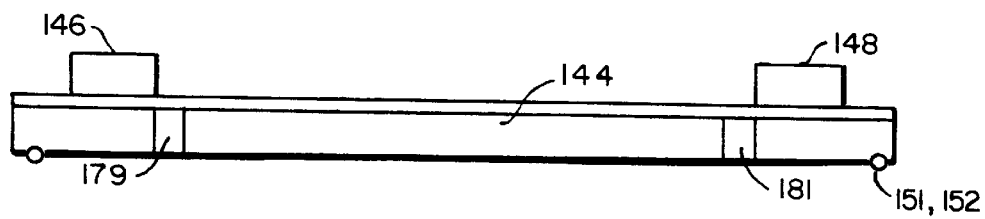
FIG. 5C is a section along line 5C—5C of the member shown in FIG. 5A.
Figure 5B:
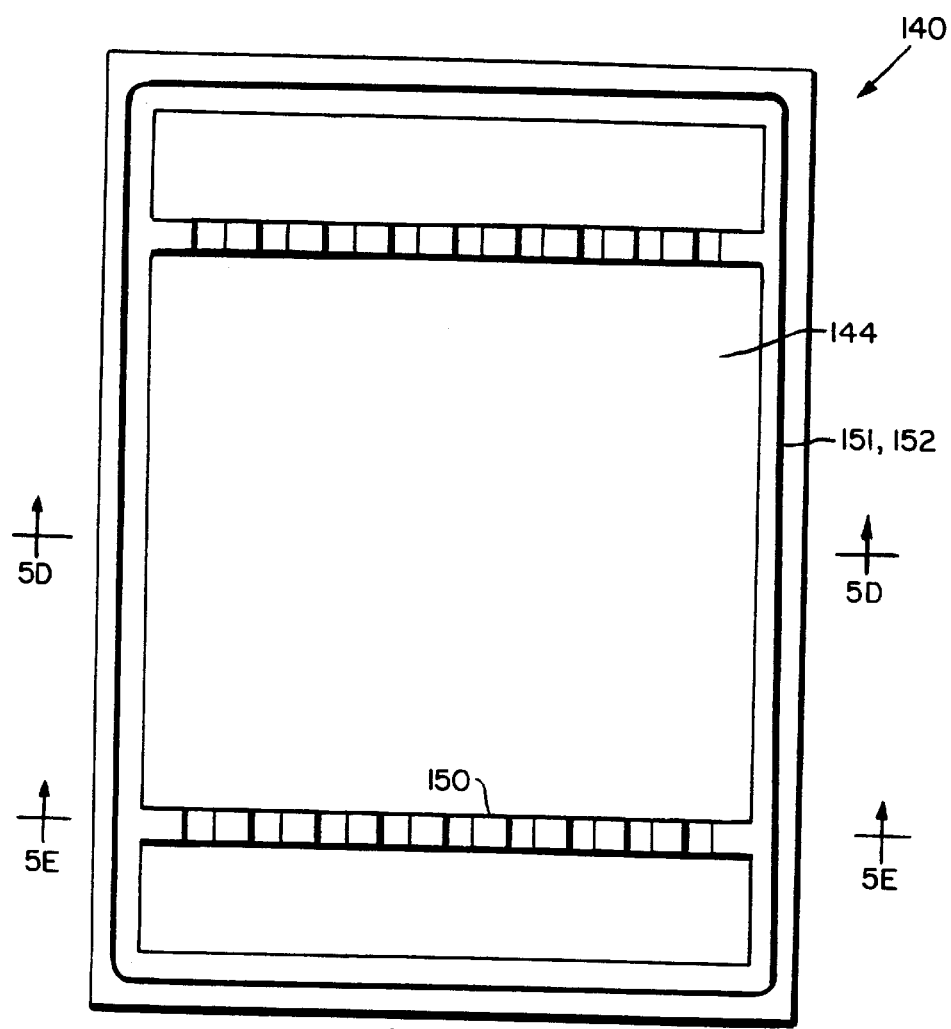
FIG. 5B is a bottom plan view of the rigid recessed member shown in FIG. 5A.
Figure 5D:
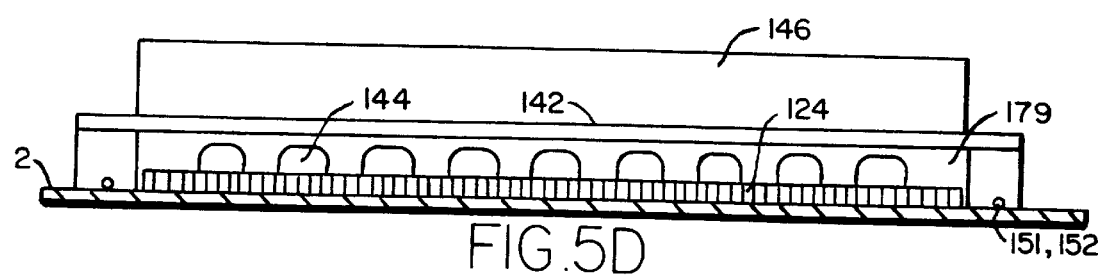
FIG. 5D is a section along line 5D—5D of the member shown in FIG. 5B disposed on surface 2 of platform 20 and further shows a gel.
Figure 5E:
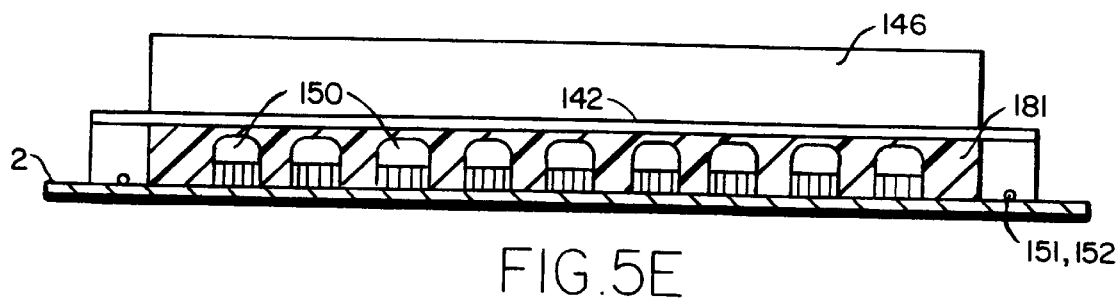
FIG. 5E is a section along line 5E—5E of the member shown in FIG. 5B.

In use, e.g., a gel casting/electrophoresis member 100 as shown in FIGS. 4A and 4B is positioned on first nonconductive surface 2 of electrophoresis platform 20, hold-down assembly 40 is moved along rails 49 to position it over the gel casting/electrophoresis or staining member of the present invention which is disposed on platform 20. Thumbscrew 42 is aligned with the margins of the gel casting/electrophoresis or staining member over the second O-ring 122 which is shown in FIG. 1G. Thumbscrew 42, is then adjusted to provide adequate pressure to hold the gel casting/electrophoresis member to electrophoresis platform 20. Hold-down assembly 40 applies pressure on the margins of the gel casting/electrophoresis member, just above the second or outer O-ring 122. Gel staining member 140 shown in FIGS. 5A and 5B can also be affixed to electrophoresis platform 20 by hold-down assembly 40.

In a particularly preferred alternate embodiment, gel casting/electrophoresis and staining members of the present invention are held to electrophoresis platform 20 by a vacuum seal and hold-down assembly 40 is not necessary.

Figure 2:
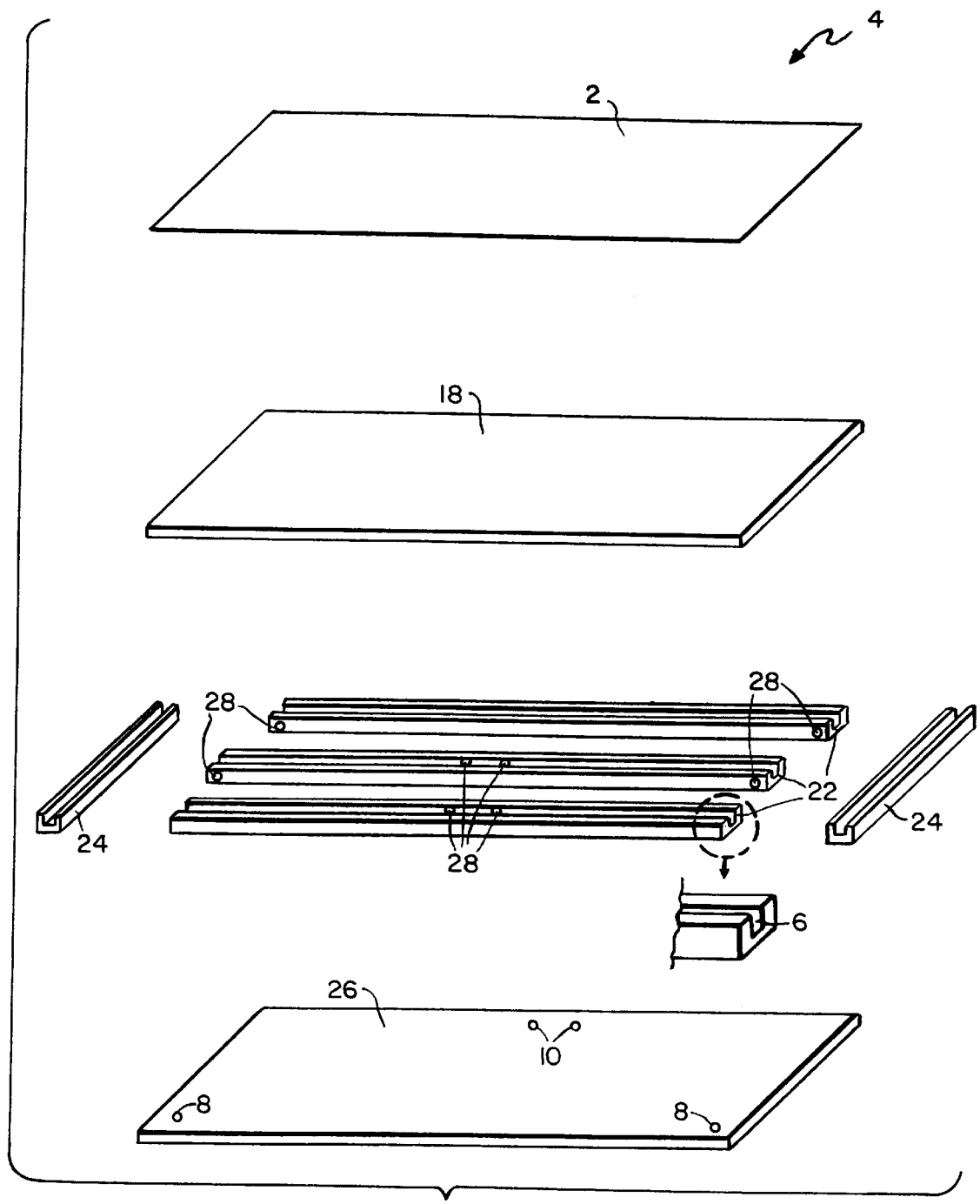
FIG. 2 is an exploded perspective view of a metal base assembly of an electrophoresis platform in accordance with the present invention showing cooling channels for containing temperature-controlled fluid.

FIG. 2 is an exploded perspective view of electrophoresis platform 20 shown in FIG. 1. FIG. 2 shows metal base assembly 4 which comprises first nonconductive surface 2, first aluminum plate 18, U-shaped aluminum channels 22, perpendicular aluminum channels 24, second aluminum plate 26, and holes in U-shaped aluminum channels 28. The temperature-control system in the embodiment shown comprises temperature cooled or heated fluid flowing through spaces provided by first aluminum plate 18, U-shaped aluminum channels 22, perpendicular aluminum channels 24, and second aluminum plate 26. Nonconductive surface 2 rests on a plate of aluminum 18 that has been machined for flatness. On the side of aluminum plate 18 opposite nonconductive surface 2 are mounted, U-shaped aluminum channels 22 to form passageways for carrying a fluid the temperature of which is controlled by a thermostat which either regulates a pump to turn on and off the flow of cooled or heated fluid or by a constant flow from a temperature-regulated bath that in this embodiment is external of the electrophoresis system to maintain the nonconductive surface 2 at a desired temperature. Fluids move both within the space defmed by U-shaped channels 22 and in the space between the channels. These passageways for fluid flow are sealed at the ends by perpendicular aluminum channels 24 which do not carry fluid and are sealed from below by a second aluminum plate 26. The edges of U-shaped channels 22 at the perimeter of aluminum plate 18 are solid and thus provide sealing along the length. The flow of liquid from one passageway to the next occurs through holes 28 drilled in the sides of U-shaped channels 22. Starting at inlet ports 8, fluid flows through the passageways in and between U-shaped channels 22 in a zig-zag fashion until it reaches outlet ports 10.

The components shown in FIG. 2 except, for nonconductive surface 2, are held together with screws (not shown) and cemented to form liquid-tight passageways. Nonconductive surface 2 is sealed in place by glass hold-down member 3 shown in FIG. 1G. Glass hold-down member 3 attaches to walls 12 around the perimeter of surface 2 and is sealed thereto with adhesive or cement, e.g., a silicone adhesive. Suitable materials for member 3 include plastic materials.

Referring now to FIG. 3, hinged mounting 52 of cradle assembly 30 allows electrophoresis platform 20 to rotate through an angle of more than 90 degrees.

Figure 3A:
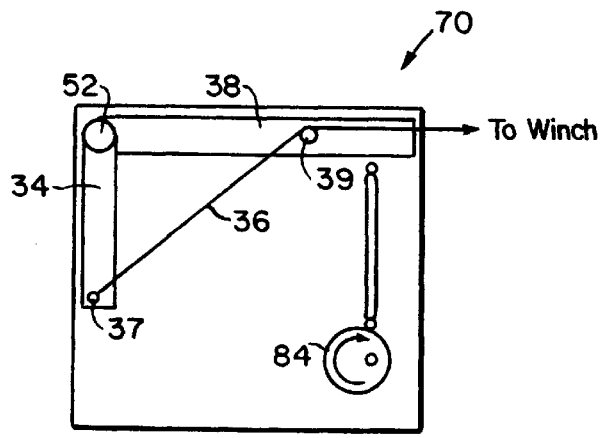
FIGS. 3A and 3B show a schematic side view of one embodiment of an electrophoresis system in accordance with the present invention, similar to that shown in FIG. 1A–C, and showing one embodiment of a lifting mechanism in accordance with the present invention.

Electrophoresis systems of the present invention can be used to carry out both one-dimensional and two-dimensional gel electrophoresis. In one-dimensional gel electrophoresis, sample wells are formed in the top of the gel by well known methods and electrophoresis is preferably carried out with electrophoresis platform 20 in a vertical position. In the case of two-dimensional gel electrophoresis, the sample is contained in a second gel which is applied to the surface of the gel by methods known to the skilled artisan with electrophoresis platform 20 in a vertical or a horizontal position or positioned between vertical and horizontal. In two-dimensional gel electrophoresis, electrophoresis can be carried out in either a vertical or horizontal position. A horizontal position is shown in FIG. 3A. A vertical position is shown in FIG. 3B.

Figure 3C:
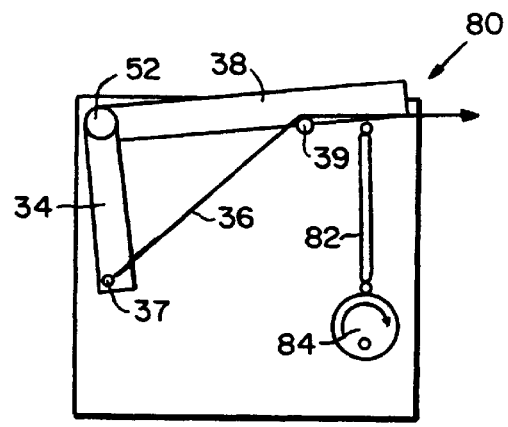
FIGS. 3C and 3D show a schematic side view of one embodiment of an electrophoresis system in accordance with the present invention, similar to that shown in FIG. 1, and showing one embodiment of an agitation member in accordance with the present invention.

A rocking motion about the horizontal position shown in FIG. 3A is preferably used for gel staining. One desired range for rocking is shown in FIGS. 3C and 3D. Rotation of electrophoresis platform 20 to an angle between horizontal and vertical can be used, if desired, to rapidly move fluids to one side of platform 20 to remove them, e.g., by aspiration, during the steps of the electrophoresis process.

In the embodiment shown in the FIG. 3, a lifting mechanism controls the motion of the cradle from the horizontal to the vertical position. An agitation mechanism rocks the cradle gently about the horizontal position.

Figure 3B:
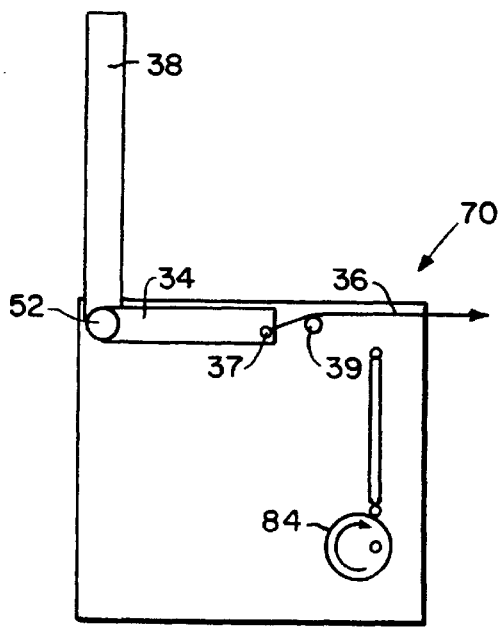
Figure 3D:
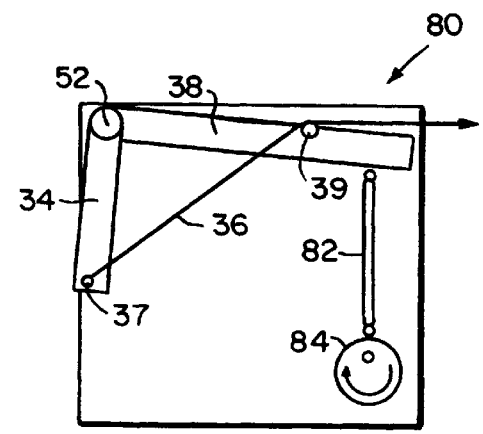

Lifting mechanism 70, in the embodiment shown in FIGS. 3A and 3B, comprises cables 36 disposed on pins 37 of arm 34. Cables 36 are made to pull on arm 34 of cradle assembly 30. Force directed to arm 34 by means of cable 36 pulling across fixed pulley 39 causes rotation of cradle assembly 30 and electrophoresis platform 20 about hinge 52. At the fully vertical position, a stop (not shown) prevents further motion, and a latch (not shown) is engaged to lock cradle assembly 30 and electrophoresis platform 20 in the vertical position. Lifting mechanism 70 can support cradle assembly 30 at any position throughout its range of motion. Lifting mechanism 70 does not interfere with the independent motion of the agitation system which is used when electrophoresis platform 20 is near the horizontal position.

Agitation mechanism 80 in the embodiment shown in FIG. 3C and 3D provides a rocking motion of cradle assembly 30 when cradle assembly 30 is near the horizontal position. Agitation mechanism 80 comprises rod 82 that is pushed upward against cradle assembly 30 by a motor-driven cam 84. The motor (not shown) has a speed control and the position of cam 84 can be varied to change the amplitude of the motion. Because rod 82 of agitation mechanism 80 is not attached to cradle assembly 30 but merely pushes against it, its action is independent of lifting mechanism 70.

Electrophoresis is carried out on one or more gels formed on nonconductive surface 2 of electrophoresis platform 20 using one or more gel casting/electrophoresis members of the present invention. One gel casting/electrophoresis member 100 of the present invention is shown in FIG. 4A to 4D. This embodiment comprises rigid recessed member 104, in preferred embodiments a plastic sheet, designed to support and maintain second nonconductive surface 102 (see FIG. 4D) in a flat position at a predetermined distance above first nonconductive surface 2 of electrophoresis platform 20. Since the surfaces must be flat for a successful gel electrophoresis, it is important that rigid recessed member 104, have sufficient stiffness to hold second nonconductive surface 102 in a flat position. Rigidity of the rigid recess member can be controlled by methods known to those skilled in the art, e.g., by selecting a material having an appropriate rigidity and thickness. In some embodiments, rigid recessed member 104 can be reinforced by known methods to achieve the desired rigidity, e.g., by use of stiffening ribs affixed to the top surface of the rigid recessed member 104.

Figure 4D:
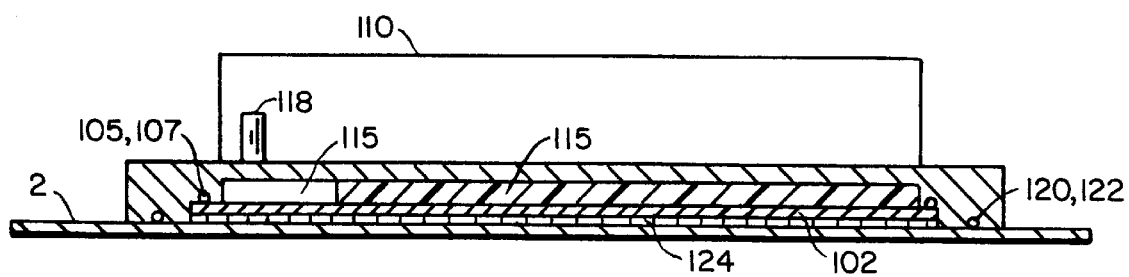
FIG. 4D is a section along line 4D—4D of the gel casting/electrophoresis member of the present invention shown in FIGS. 4A, 4B and 4C, disposed on the first nonconductive surface of an electrophoresis platform. In the embodiment shown in FIG. 4D a gel has been cast and polymerized in the space formed between a gel casting/electrophoresis member and the first nonconductive surface of an electrophoresis platform.

In preferred embodiments, second nonconductive surface 102 is a glass plate. Rigid recessed member 104 is provided with slot 106 near the bottom edge and a larger rectangular opening 108 near the top edge. Slot 106 and opening 108 in rigid recessed member 104 are enclosed by upper electrode buffer chamber 110 and lower electrode buffer chambers 112 as shown schematically in FIG. 4C. Rigid recessed member 104 is provided with recess 126 for receiving glass plate 102 as shown in FIGS. 4B and 4D. Groove 105 is disposed around the perimeter of recess 126 to receive O-ring 107. When glass plate 102 is disposed in recess 126, the top of glass plate 102 is still recessed relative to rigid recessed member 104 by the predetermined gel thickness. In the embodiment shown, glass plate 102 is flush with lower slot perimeter surface 106A which surrounds slot 106. Disposed in recess 126 are cooling channels 114 formed by plastic strips 115 and connected to inlet 116 and outlet 118 ports for a temperature controlled liquid. When glass plate 102 is disposed in recess 126 and a vacuum is pulled, O-ring 107 disposed in O-ring groove 105 makes a seal and glass plate 102 is held against cooling channels 114 by a vacuum which is pulled by means of a vacuum pump attached to outlet port 118 while closing inlet port 116 or vice versa.

Rigid recessed member 104 is provided with second O-ring groove 120 for receiving O-ring 122. O-ring 122 is capable of providing sealing contact between gel casting/electrophoresis member 100 and nonconductive surface 2 of electrophoresis platform 20 when member 100 is disposed thereon. In forming and running a gel in the embodiment of gel casting/electrophoresis member 100 shown in FIGS. 4A to 4D, member 100 is clamped to electrophoresis platform 20 using hold-down assemblies 40 as shown in FIG. 1G. Glass plate 102 is not affixed to gel casting/electrophoresis member 100 but is held in recess 126 of rigid recessed member 104 by vacuum and, after polymerization, by the gel itself. After polymerization, the vacuum is released and inlet port 116 and outlet port 118 are connected to a means (not shown) to provide and circulate cooling fluid. Cooling fluid is drawn through the apparatus under slight negative pressure. This design allows glass plate 102 to remain flat even during temperature changes which may expand or contract glass plate 102 and plastic member 104 at different rates. Gel casting/electrophoresis member 100 provides for convenient removal of glass plate 102 for cleaning.

During gel casting, electrophoresis platform 20 is placed in a vertical position as shown in FIG. 3B. Slot 106 is closed by a sealant such as tape (not shown). Gel casting/electrophoresis member 100 has sufficient rigidity to maintain the predetermined gel space formed between glass plate 102 and first nonconductive surface 2 of electrophoresis platform 20 without bending in response to the weight of the unpolymerized gel. Before gel electrophoresis, sealant on the upper side of the gel casting/electrophoresis member is removed from slot 106. If the sealant is on the under side of rigid recessed member 104, it is slit by cutting through slot 106 to provide communication with lower buffer chamber 112. With electrophoresis platform 20 in a horizontal position as shown in FIG. 3A, electrode buffers are added to upper and lower buffer chambers 110,112. In this embodiment, gel 124 extends beyond glass plate 102 to cover lower slot perimeter surface 106A. However, gel 124 is removed from slot 106 as shown in FIG. 1G before conducting electrophoresis.

Figure 4E:
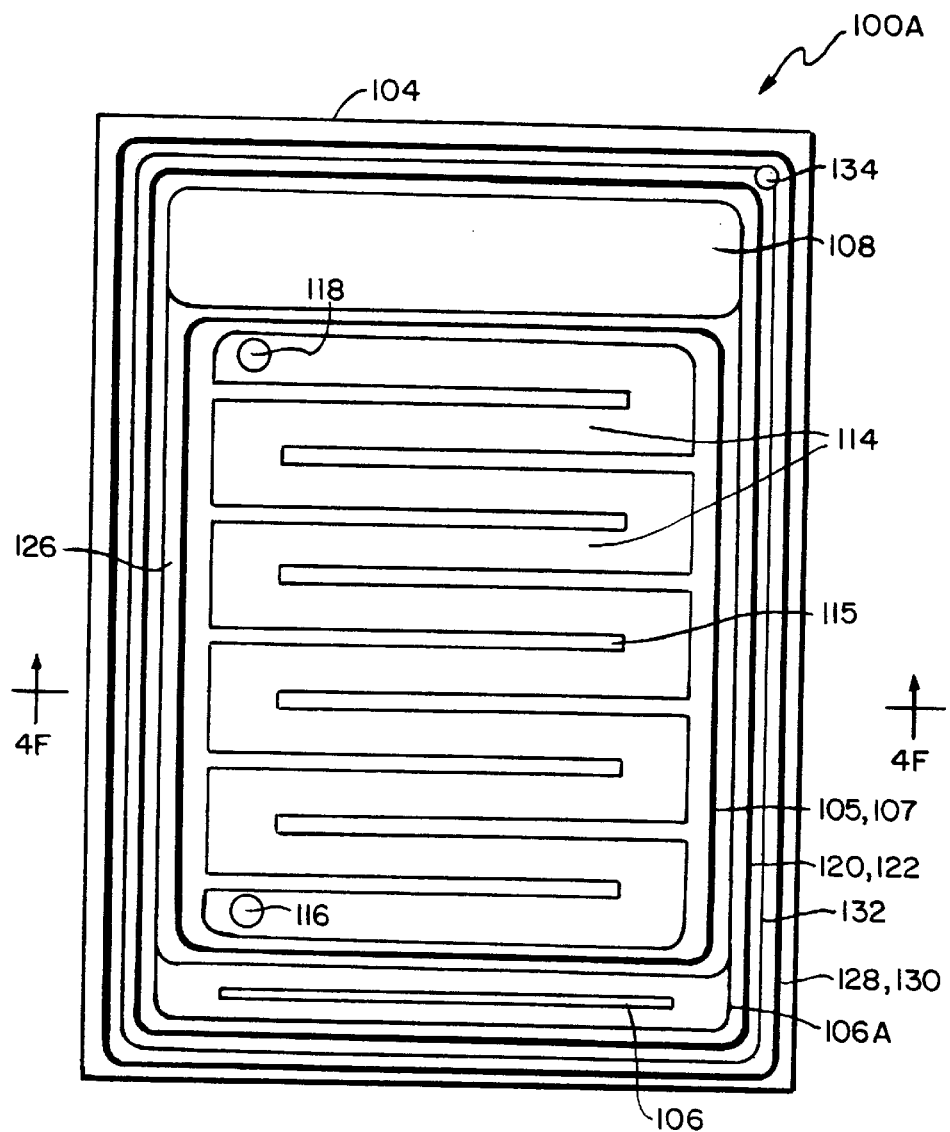
FIG. 4E shows a bottom plan view of another preferred embodiment of a gel casting/electrophoresis member of the present invention.
Figure 4F:
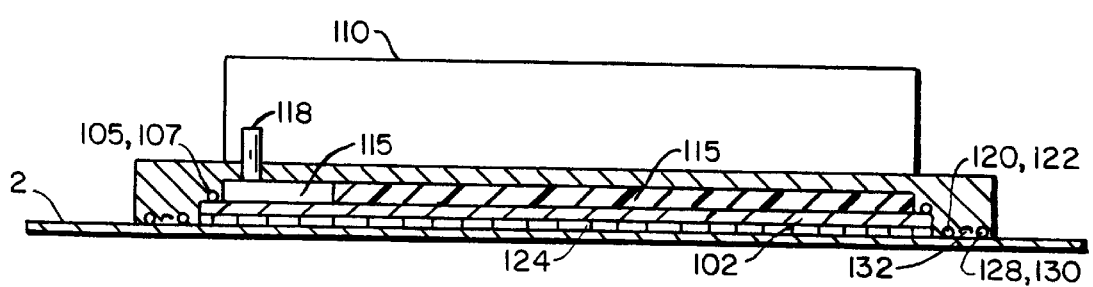
FIG. 4F is a section along line 4F—4F of the gel casting/electrophoresis member shown in FIG. 4E wherein it is sealably affixed to the first nonconductive surface of an electrophoresis platform of the present invention and includes therein a gel.

An alternative embodiment of a gel casting/electrophoresis member of the present invention is shown in FIGS. 4E and 4F. Gel casting/electrophoresis member 100A shown in FIGS. 4E and 4F is adapted for sealable attachment to electrophoresis platform 20 by vacuum. This embodiment is similar to the embodiments shown in FIGS. 4A through 4D. However, outer perimeter of rigid recessed member 104 is provided with two concentric grooves 120,128 for receiving O-rings 122,130 respectively. Between O-ring groove 120 and 128 is disposed vacuum groove 132. Port 134 for connection to, e.g., a vacuum pump, is disposed in rigid recessed member 104 over vacuum groove 132 to enable a vacuum to be pulled on gel casting/electrophoresis member 100A, thereby sealing it to nonconductive surface 2 of electrophoresis platform 20.

One preferred gel staining member 140 in accordance with the present invention is shown in FIG. 5. In use, staining member 140 is clamped over a gel on nonconductive surface 2 of electrophoresis platform 20 to confine the gel within a limited volume for purposes of gel staining. Staining member 140 comprises rigid recessed member 142 of plastic or other nonconductive material. Member 142 has sufficient thickness to enable formation of containment recess 144 therein to trap a gel when gel staining member 140 is removably sealed to nonconductive surface 2 of electrophoresis platform 20. Containment recess 144 is bounded at both ends by gel retainer strips 179,181 which are provided with channels 150 (see FIG. 5E). In the embodiment shown, rigid recessed member 142 is provided with two end reservoirs 146,148 preferably of equal volume to hold staining fluids, and communicating channels 150 in gel retainer strips 179,181 that allow fluid to pass between gel containment space 144 and reservoirs 146,148. Rigid recessed member 142 is provided with O-ring groove 151 to receive O-ring 152 which is used to seal staining member 140 to nonconductive surface 2 of electrophoresis platform 20 when pressure is applied by hold-down assemblies 40. In other preferred embodiments, staining member 140 is configured for vacuum attachment to electrophoresis platform 20, e.g., in a manner similar to that shown for affixing gel casting/electrophoresis member 100A in FIGS. 4E and 4F.

In another preferred embodiment, staining is carried out as electrophoresis platform 20 is rocked by agitation assembly 80. Changing of staining fluid is carried out by lifting electrophoresis platform 20 to an angle between horizontal and vertical and removing fluids from the front reservoir 148 by aspiration. Gel staining can also be carried out on electrophoresis platform 20 without use of a staining member. In the case of the embodiment shown in the Figures, walls 12 of electrophoresis platform 20 contain staining fluids provided thereto. In this method, the platform is used as a large tray which can accommodate one or more gels in the same volume of staining fluids. This method requires no additional apparatus but requires the use of larger volumes of fluids. Gels on electrophoresis platform 20 can be distinguished by small notches placed in their corners.

Figure 6A:
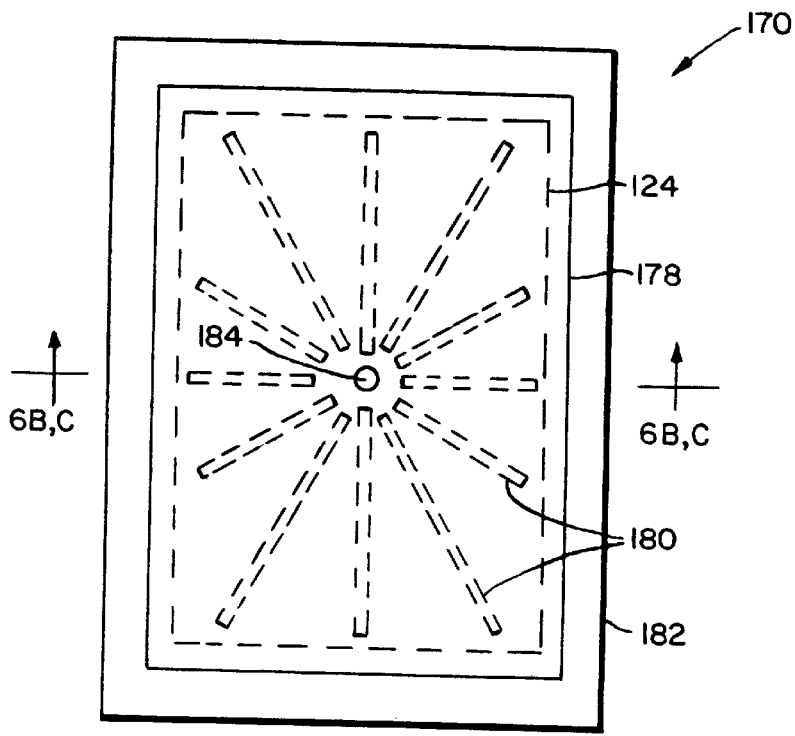
FIG. 6A shows a top plan view of one gel drying member in accordance with the present invention.
Figure 6B:
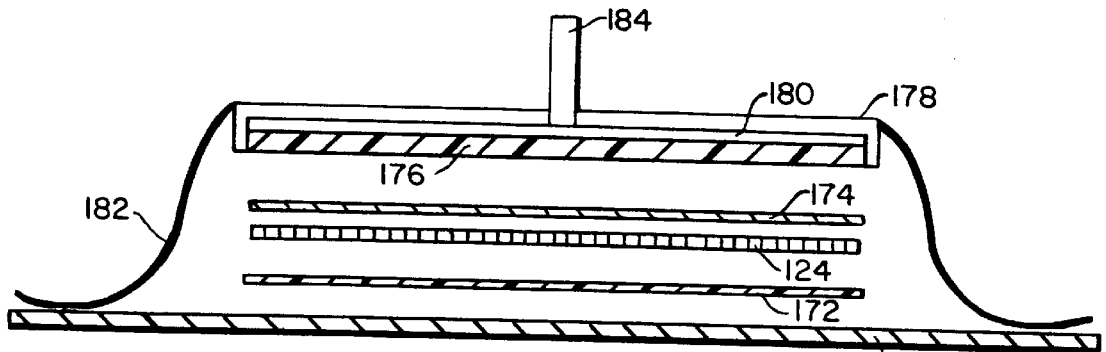
FIG. 6B is an exploded section along line 6B—6B of the gel drying member shown in FIG. 6A together with the first nonconductive surface of an electrophoresis platform of the present invention having disposed thereon a gel.
Figure 6C:
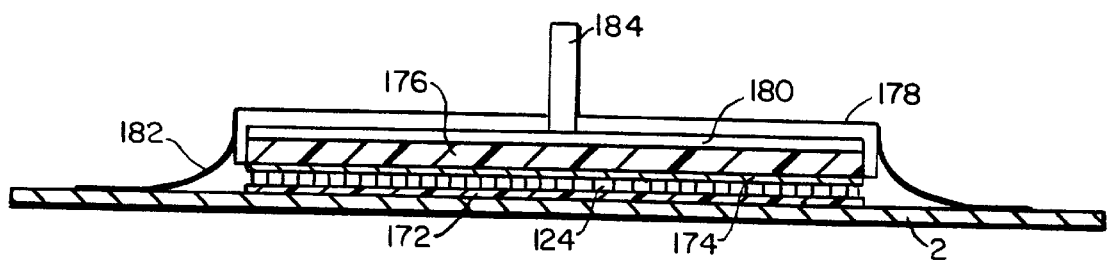
FIG. 6C shows an exploded section along line 6B—6B view of the member shown in FIG. 6B collapsed.

Gels can be dried on electrophoresis platform 20 if desired, by use of a gel drying member of the present invention. One embodiment of such a gel drying member is shown in FIG. 6. Referring now to FIG. 6, gel drying member 170 comprises porous plastic sheet 176, rigid plastic sheet 178, channels 180 disposed in rigid plastic sheet 178 and open to porous plastic sheet 176 when in contact therewith, silicon rubber sheet 182, and port 184.

To prepare the gel for drying, thin sheet of nonadhesive material 172 is placed under gel 124 disposed on nonconductive surface 2 of electrophoresis platform 20 while it is immersed in liquid such as water. Excess liquid is removed from electrophoresis platform 20 by aspiration and drying paper 174 is placed on gel 124. Porous plastic sheet 176 is placed over paper 174, rigid plastic sheet 178 is placed over porous plastic sheet 176 with channels 180 facing sheet 176. Rubber sheet 182 is attached to rigid plastic sheet 178 as a skirt.

When pressed to nonconductive surface 2 of electrophoresis platform 20, rubber sheet 182 seals the vacuum within the drying member. A vacuum is pulled at port 184 thereby drawing vacuum through porous plastic sheet 176. During drying, heat is applied to gel 124 by circulating heated fluid through channels 6 of electrophoresis platform 20. An alternate method is to apply heat directly to the metal of the electrophoresis platform using thermostat-regulated heat tapes. Drying member 170 is not clamped rigidly to electrophoresis platform 20, but is held on nonconductive surface 2 only by the vacuum seal. Silicone rubber sheet 182 forms a flexible seal so that as gel 124 dries and becomes thinner, gel drying member 170 moves closer to electrophoresis platform 20 and remains in contact with gel 124.

By following the teachings of the present invention, the components of the electrophoresis system of the present invention are made from materials and by techniques known to those of ordinary skill in the art. To ensure simple manufacture of the electrophoresis systems of the present invention, it is advantageous to use readily processable plastic where suitable.

It will be apparent to the skilled artisan in light of the teachings of the present invention that configurations of electrophoresis platform 20, cradle assembly 30, hold-down assembly 40 and support frame 50, lifting mechanism 70, agitation assembly 80 other than those shown may be utilized without departing from the spirit and scope of the present invention. The same is true for gel casting/ electrophoresis member 100, staining member 140 and gel drying member 170.

As is amply illustrated by the various embodiments in accordance with the present invention described herein, by following the teachings of the present invention one of ordinary skill in the art can vary the disclosed electrophoresis system and structure by utilizing ordinary skill in the art to meet the demands of a particular application and situation. Thus, it is understood that the examples and embodiments described herein are for illustrative purposes only and that various modifications or changes in light thereof that will be suggested to persons skilled in the art are to be included in the spirit and purview of this application and the scope of the approved claims.

What is claimed:

1. An apparatus for forming at least one gel and for conducting electrophoresis on the gel without removing the gel from the apparatus, wherein the apparatus comprises an electrophoresis platform defining a first nonconductive surface, wherein the electrophoresis platform (i) is adapted to move between horizontal and vertical positions, and (ii) is adapted to receive in sealing disposition on the first nonconductive surface at least one removable gel casting/ electrophoresis member defining a second nonconductive surface, wherein the gel casting/electrophoresis member defines at least one space between the first and second nonconductive surfaces for forming at least one gel, wherein the gel casting/electrophoresis member will move between horizontal and vertical as one with the electrophoresis platform as the eletrophoresis platform is moved.

2. The apparatus of claim 1, wherein said electrophoresis platform is adapted to move through at least 90 degrees.

3. The apparatus of claim 1, wherein said electrophoresis platform is adapted to receive multiple gel casting/ electrophoresis members.

4. The apparatus of claim 1, wherein said electrophoresis platform is adapted to receive at least one removable gel staining member defining a third surface for staining the gel after electrophoresis has been conducted without removing the gel from the system, wherein the gel staining member when sealably disposed on the first nonconductive surface over a gel disposed thereon, defines a space between the third surface and the gel for containing a staining agent for the gel.

5. The apparatus of claim 4, wherein said first and second nonconductive surfaces comprise glass and/or plastic.

6. The apparatus of claim 1, wherein the electrophoresis platform is adapted to move in or on a support structure.

7. An apparatus for forming at least one gel and for conducting electrophoresis on the gel without removing the gel from the apparatus, wherein the apparatus comprises:

(a) an electrophoresis platform defining a first nonconductive surface; wherein the electrophoresis platform is adapted to move between horizontal and vertical positions;

(b) at least one gel casting/electrophoresis member defining a second nonconductive surface and adapted for removable and sealable attachment to the first nonconductive surface, wherein the gel casting/electrophoresis member in sealing disposition on the first nonconductive surface defines at least one space between the first and second nonconductive surfaces for forming at least one gel, wherein the gel casting/electrophoresis member will move between horizontal and vertical as one with the electrophoresis platform as the electrophoresis platform is moved, and, further wherein the gel casting/ electrophoresis member comprises a first end and a second end, the second end being lower than said first end when the electrophoresis platform is in a vertical position;

(c) at least one first buffer chamber capable of communicating with the first end and at least one second buffer chamber capable of communicating with the second end; and (d) at least one first and second electrodes for the first and second buffer chambers respectively, the electrodes connectable to a power supply for establishing an electromotive force for inducing electrophoretic action.

8. The apparatus of claim 7, wherein said electrophoresis platform is adapted to move through at least 90 degrees.

9. The apparatus of claim 7, wherein said first and second nonconductive surfaces comprise glass and/or plastic.

10. The apparatus of claim 7, wherein both said first and second nonconductive surfaces comprise a layer of glass.

11. The apparatus of claim 10, further comprising a metal layer disposed behind the first glass layer.

12. The apparatus of claim 7, wherein said gel casting/electrophoresis member further comprises a holding member in which the second nonconductive surface is disposed and wherein the holding member is provided with a resilient fluid-impermeable material disposed adjacent and surrounding the perimeter of the second nonconductive surface, the resilient fluid-impermeable material being capable of providing sealing contact with the first nonconductive surface.

13. The apparatus of claim 12, wherein said resilient fluid-impermeable material comprises a continuous gasket.

14. The apparatus of claim 7, further comprising a cooling system to regulate the temperature of the first and second nonconductive surfaces.

15. The apparatus of claim 14, wherein said cooling system comprises the circulation of heat transfer fluid adjacent the first and second nonconductive surfaces.

16. The apparatus of claim 7, further comprising an agitation system to move the electrophoresis platform in a predetermined manner.

17. The apparatus of claim 16, wherein said agitation system moves the electrophoresis platform in a rocking and/or oscillatory manner.

18. The apparatus of claim 7, wherein both said first and second ends of the gel casting/electrophoresis member are provided with at least one opening to provide communication among the gel, the first and second buffer chambers and the electrodes.

19. The apparatus of claim 18, wherein said opening in the second end is removably sealable.

20. The apparatus of claim 7, further comprising at least one gel staining member for staining the gel after electrophoresis has been conducted without removing the gel from the apparatus, the gel staining member defining a third surface and adapted for removable and sealable attachment over at least one gel disposed on the first surface, wherein the gel staining member in sealing disposition on the first surface over the gel defines a space between the first nonconductive surface and the third surface for containing a staining agent for the gel, and further wherein the gel staining member comprises a first and a second end.

21. The apparatus of claim 20, wherein said gel staining member further comprises a plastic sheet having disposed therein a central hollow area defining the third surface.

22. The apparatus of claim 21, wherein said gel staining member further comprises a first staining agent reservoir chamber communicating with the first end and a second staining agent reservoir chamber communicating with the second and, further wherein, both staining agent reservoir chambers communicate with the central hollow area defining the third surface.

23. The apparatus of claim 7, further comprising at least one gel drying member for drying at least one gel after electrophoresis has been conducted without removing the gel from the apparatus, the gel drying member defining a water permeable surface and configured for removable and sealable attachment over at least one gel disposed on the first nonconductive surface, wherein the permeable surface of the gel drying member when sealably disposed on the first nonconductive surface over the gel contacts the gel.

24. The apparatus of claim 23, wherein said gel drying member further comprises a rigid plastic sheet disposed over the permeable surface, the plastic sheet comprising at least one port open to the permeable surface and to the atmosphere.

25. The apparatus of claim 24, wherein said gel drying member further comprises a non-rigid seal around the perimeter of the rigid plastic sheet, the seal being capable of providing a seal between the rigid plastic sheet and the first nonconductive surface.

26. The apparatus of claim 7, wherein the electrophoresis platform is adapted to move in or on a support structure.

27. An electrophoretic method comprising:
(a) forming a gel in an electrophoresis apparatus, wherein the apparatus comprises:
   i) an electrophoresis platform defining a first nonconductive surface, wherein the electrophoresis platform is adapted to move between horizontal and vertical positions;
   ii) at least one gel casting/electrophoresis member defining a nonconductive second surface, wherein the gel casting/electrophoresis member is sealably disposed on the first nonconductive surface to define a space between the first and second nonconductive surfaces for forming the gel, wherein the gel casting/electrophoresis member will move between horizontal and vertical as one with the electrophoresis platform as the electrophoresis platform is moved, and wherein the gel casting/electrophoresis member comprises a first end and a second end;
   iii) at least one first buffer chamber adapted to communicate with the first end and at least one second buffer chamber adapted to communicate with the second end; and
   iv) at least one first and second electrodes for the first and second buffer chambers respectively, the electrodes adapted to connect to a power supply for establishing an electromotive force sufficient to induce electrophoretic action;
wherein
(a) the gel is formed between the first and second surfaces and the electrophoresis platform is disposed in a vertical position;
(b) applying the mixture to be separated to the gel; and
(c) separating the mixture by electrophoresis.

28. The method of claim 27, wherein the method further comprises the step of positioning said electrophoresis platform in a horizontal position or a position between horizontal and vertical between steps (a) and (b).

29. The method of claim 27, wherein the method further comprises the step of positioning said electrophoresis platform in a horizontal position or a position between horizontal and vertical between steps (b) and (c).

30. The method of claim 27 further comprising:
(a) removing the gel/casting electrophoresis member from the first non-conductive surface;
(b) staining the gel in the electrophoresis apparatus, wherein the apparatus further comprises; at least one gel staining member for staining the gel after electrophoresis has been conducted without removing the gel from the system, the gel staining member defining a third surface and configured for removable and sealable attachment on the first nonconductive surface, wherein the gel staining member when sealably disposed on the first nonconductive surface defines a space between the first nonconductive surface and third surface for containing a staining agent for the gel, and further wherein the gel staining member comprises a first and a second end; and wherein the gel staining member is sealably disposed over a gel disposed on the first nonconductive surface; and (c) providing at least one staining agent to the space between the first nonconductive surface and the third surface.

31. The method of claim 27 further comprising:

(a) removing the gel staining member;

(b) drying the gel in the electrophoresis apparatus, wherein the apparatus further comprises at least one gel drying member for drying the gel after electrophoresis has been conducted without removing the gel from the system, the gel drying member defining a water permeable surface and configured for removable and sealable attachment on the first nonconductive surface, wherein the water permeable surface of the gel drying member when sealably disposed on the first nonconductive surface over a gel contacts the gel;

wherein gel drying member is sealably disposed over a gel disposed on the first nonconductive surface wherein the water permeable surface contacts the gel; and (c) providing heat and vacuum to the gel to cause water to pass from the gel through the water permeable surface.

32. The method of claim 27, wherein the electrophoresis platform is adapted to move in or on a support structure.

33. An electrophoretic method comprising:

(a) forming a gel in an electrophoresis apparatus, wherein the apparatus comprises:

i) an electrophoresis platform defining a first nonconductive surface, wherein the electrophoresis platform is adapted to move between horizontal and vertical positions;

ii) at least one gel casting/electrophoresis member defining a second nonconductive surface adapted to provide a removable and sealable attachment to the first nonconductive surface, wherein the gel casting/electrophoresis member when sealably disposed on the first nonconductive surface defines a space between the first and second nonconductive surfaces for forming the gel, wherein the gel casting/electrophoresis member will move between horizontal and vertical as one with the electrophoresis platform as the electrophoresis platform is moved, and, further wherein the gel casting/electrophoresis member comprises a first end and a second end, the second end being lower when the electrophoresis platform is positioned vertically;

iii) at least one first buffer chamber adapted to communicate with the first end and at least one second buffer chamber adapted to communicate with the second end;

iv) at least one first and second electrodes for the first and second buffer chambers respectively, the electrodes adapted to connect to a power supply sufficient to establish an electromotive force to induce electrophoretic action; and v) at least one gel staining member defining a third surface adapted to provide a removable and sealable attachment to the first nonconductive surface, wherein the gel staining member when sealably disposed on the first surface over a gel defines a space between the first nonconductive surface and the third surface adapted to contain a staining agent for the gel;

wherein at least one gel is formed between the first and second nonconductive surfaces of the system, and wherein the electrophoresis platform is disposed in a vertical position;

(b) applying the mixture to be separated to the gel;

(c) separating the mixture by electrophoresis;

(d) removing the gel casting/electrophoresis member from the electrophoresis platform while it is in a horizontal position;

(e) sealably disposing the gel staining member on the first nonconductive surface over at least one gel; and (f) providing one or more staining agents sequentially to the gel staining member.

34. The method of claim 33, wherein the method further comprises the step of positioning the electrophoresis platform in a horizontal position or a position between horizontal and vertical between steps (b) and (c).

35. The method of claim 33, wherein the method further comprises the step of positioning the electrophoresis platform in a horizontal position or a position between horizontal and vertical between steps (b) and (c).

36. The method of claim 33, wherein the method further comprises:

(g) agitating the electrophoresis platform to facilitate staining, wherein the apparatus further comprises an agitation system to move the electrophoresis platform in a predetermined manner.

\* \* \* \* \*